(12) United States Patent
Toyoshima et al.

(10) Patent No.: US 7,947,707 B2
(45) Date of Patent: May 24, 2011

(54) NITROGENATED HETEROCYCLIC COMPOUND AND PHARMACEUTICAL COMPOSITION COMPRISING THE SAME

(75) Inventors: Takahiro Toyoshima, Ibaraki (JP); Toshinobu Sasaki, Tokyo (JP); Chikara Hoshino, Tokyo (JP); Masakazu Takeda, Tokyo (JP)

(73) Assignee: Kissei Pharmaceutical Co., Ltd., Matsumoto-Shi, Nagano (JP)

( * ) Notice: Subject to any disclaimer, the term of this patent is extended or adjusted under 35 U.S.C. 154(b) by 254 days.

(21) Appl. No.: 12/089,518

(22) PCT Filed: Oct. 3, 2006

(86) PCT No.: PCT/JP2006/319806
§ 371 (c)(1),
(2), (4) Date: Apr. 7, 2008

(87) PCT Pub. No.: WO2007/043401
PCT Pub. Date: Apr. 19, 2007

(65) Prior Publication Data
US 2009/0306396 A1    Dec. 10, 2009

(30) Foreign Application Priority Data
Oct. 7, 2005 (JP) .................................. 2005-295429

(51) Int. Cl.
| A61K 31/437 | (2006.01) |
| A61K 31/4155 | (2006.01) |
| A61K 31/4162 | (2006.01) |
| A61K 31/4192 | (2006.01) |
| C07D 221/00 | (2006.01) |
| C07D 231/56 | (2006.01) |
| C07D 207/00 | (2006.01) |
| C07D 209/04 | (2006.01) |
| C07D 231/10 | (2006.01) |
| C07D 403/00 | (2006.01) |

(52) U.S. Cl. ........ 514/300; 546/112; 514/359; 514/405; 514/406; 514/408; 514/410; 548/361.1; 548/400; 548/469; 548/373.1; 548/255

(58) Field of Classification Search .................. 514/300, 514/359, 405, 406, 408, 410; 546/112; 548/361.1, 548/400, 469, 373.1, 255
See application file for complete search history.

(56) References Cited

U.S. PATENT DOCUMENTS

| 3,786,061 A | 1/1974 | Novello et al. |
| 5,614,520 A | 3/1997 | Kondo et al. |
| 6,015,829 A | 1/2000 | Ishibuchi et al. |
| 2004/0127492 A1 | 7/2004 | Vazquez et al. |
| 2005/0004175 A1 | 1/2005 | Nakamura et al. |
| 2005/0176796 A1 | 8/2005 | D'Alessio et al. |
| 2009/0306396 A1 | 12/2009 | Toyoshima et al. |
| 2010/0056521 A1 | 3/2010 | Shimizu et al. |

FOREIGN PATENT DOCUMENTS

| AU | 2004200420 A1 | 9/2004 |
| CA | 2682393 A1 | 10/2008 |
| JP | 2000-1431 A | 1/2000 |
| JP | 2002-105067 A | 4/2002 |
| JP | 3399559 B2 | 4/2003 |
| WO | 92 09279 A1 | 6/1992 |
| WO | 98 18765 A1 | 5/1998 |
| WO | 03 064410 A1 | 8/2003 |
| WO | 03 070236 A2 | 8/2003 |
| WO | 2007/043400 A1 | 4/2007 |
| WO | 2008/126898 A1 | 10/2008 |
| WO | 2008/126899 A1 | 10/2008 |
| WO | 2008/126901 A1 | 10/2008 |

OTHER PUBLICATIONS

Golub et al. Science (1999), vol. 286 531-537.*
Lala et al. Cancer and Metastasis Reviews (1998), 17(1), 91-106.*
"Alzheimer's Drugs." URL: http://www.cnn.com/HEALTH/mentalhealth/alzheimers/#, Entered Oct. 9, 2010.*
International Search Report of PCT/JP2006/319806, date of mailing: Jan. 30, 2007.

\* cited by examiner

Primary Examiner — Rebecca L Anderson
Assistant Examiner — Samantha L Shterengarts
(74) Attorney, Agent, or Firm — Westerman, Hattori, Daniels & Adrian, LLP

(57) ABSTRACT

The present invention relates to novel compounds having a xanthine oxidase inhibitory effect and an uricosuric effect and pharmaceutical compositions comprising the same as an active ingredient. That is, the present invention relates nitrogen-containing heterocyclic compounds represented by the following general formula (I):

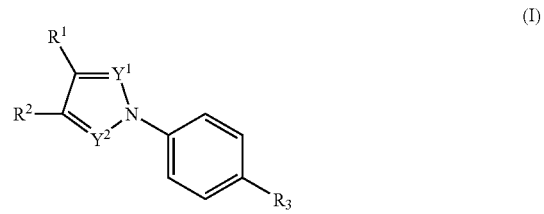

(I)

wherein $Y^1$ represents N or $C(R^4)$; $Y^2$ represents N or $C(R^5)$; $R^4$ and $R^5$ independently represent an alkyl group, a hydrogen atom etc.; one of $R^1$ and $R^2$ represents an optionally substituted aryl group, an alkoxy group or an optionally substituted heterocyclic group; the other of $R^1$ and $R^2$ represents a haloalkyl group, a cyano group, a halogen atom etc.; and $R^3$ represents a 5-tetrazolyl group or a carboxy group, and pharmaceutically acceptable salts thereof, and pharmaceutical compositions comprising the same as an active ingredient.

12 Claims, No Drawings

NITROGENATED HETEROCYCLIC COMPOUND AND PHARMACEUTICAL COMPOSITION COMPRISING THE SAME

TECHNICAL FIELD

The present invention relates to nitrogen-containing heterocyclic compounds and pharmaceutical compositions containing the same. More particularly, the present invention relates to nitrogen-containing heterocyclic compounds having a xanthine oxidase inhibitory effect and an uricosuric effect and pharmaceutical compositions containing the same.

BACKGROUND ART

The major causes of hyperuricemia are increased production and decreased excretion of uric acid. The former is mainly caused by overproduction of uric acid by xanthine oxidase (hereinafter also referred to as X.O.). On the other hand, the latter is increased renal tubular reabsorption of uric acid and the main mechanism is upregulation of human uric acid transporter (hereinafter also referred to as URAT1). Since uric acid is slightly soluble in water, that causes hyperuricemia. When uric acid in blood gets excessive, crystalline uric acid precipitates in the joints and so on and that causes an acute attack of arthritis (gout) or chronic changes in bones and joints. Furthermore, complications such as urinary calculi and renal insufficiency (gouty kidney) become, a problem.

Currently, as therapeutic agents for gout and hyperuricemia, allopurinol, a X.O. inhibitor, is widely used. In addition, other therapeutic agents for hyperuricemia having a X.O. inhibitory effect are disclosed in Patent references 1 to 4. Benzbromarone having an inhibitory effect of uric acid reabsorption (an uricosuric effect) is also used. As another agent, probenecid is illustrated, but it is not frequently used due to its weak activity. In addition, biaryl compounds or diaryl ether compounds described in Patent reference 5 are reported as agents having an uricosuric effect.

[Patent reference 1] Japanese Patent No. 3399559 specification.
[Patent reference 2] Japanese Patent No. 3220987 specification.
[Patent reference 3] Japanese Patent Publication No. 2002-105067 gazette.
[Patent reference 4] International Publication No. WO03/064410 pamphlet.
[Patent reference 5] Japanese Patent Publication No. 2000-001431 gazette.

DISCLOSURE OF THE INVENTION

Problem that the Invention Aims to Solve

However, regarding allopurinol of a X.O. inhibitor, oxypurinol, a methanolic product, can be accumulated in a body, and adverse effects such as rash, deterioration of renal function, hepatitis and the like have been reported, and thus, it is not always an easy-to-use agent. In addition, regarding benzbromarone which has an inhibitory effect of uric acid reabsorption (an uricosuric effect), severe adverse effects such as fulminant hepatitis are reported and calculi can be caused. Therefore, proper limited use is required, and it is not always an easy-to-use agent. On the other hand, clinical benefits of the therapeutic agents for hyperuricemia having a X.O. inhibitory effect described in Patent references 1 to 4 are still uncertain. Pharmacological effects of the biaryl compounds or diary ether compounds described in Patent reference 5 seem weaker than existing products. Most of therapeutic agents in the technical field have been sold for a few decades, and in order to broaden treatment options, a new therapeutic agent has been still desired in the medical field.

Therefore, the objective of the present invention is to provide a novel compound having a X.O. inhibitory effect and an uricosuric effect, and a pharmaceutical composition comprising as an active ingredient the same.

Means to Solve the Problem

The present inventors have studied earnestly to solve the above problem and finally found that a certain nitrogen-containing heterocyclic compound having a specific structure has a X.O. inhibitory effect and an uricosuric effect, thereby forming the basis of the present invention.

That is, the present invention relates to:

[1] a nitrogen-containing heterocyclic compound represented by the following general formula (I):

[Chem. 1]

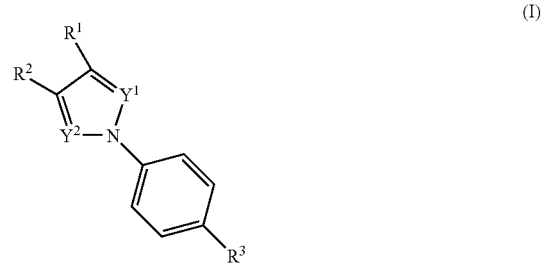

(I)

wherein $Y^1$ represents N or $C(R^4)$; $Y^2$ represents N or $C(R^5)$; $R^4$ and $R^5$ independently represents an alkyl group which may have a halogen atom, a hydrogen atom, a halogen atom, a cyano group or an alkoxy group; one of $R^1$ and $R^2$ represents an haloalkyl group, a cyano group, a carbamoyl group or a halogen atom; the other of $R^1$ and $R^2$ represents an aryl group which may have a substituent selected from the group consisting of an alkyl group, a haloalkyl group, an alkoxy group and a halogen atom in which some of the substituents may form a ring, an alkoxy group or a heterocyclic group selected from the group consisting of a thienyl, thiazolyl or pyrrolyl group which may be substituted by an alkyl group or a halogen atom; and $R^3$ represents a 5-tetrazolyl group or a carboxy group; and with the proviso that when $Y^2$ represents $CR^5$, $Y^2$ may form a benzene or pyridine ring which may have a haloalkyl group, a halogen atom, a cyano group or an alkoxy group as a substituent together with $R^2$, and some of the neighboring substituents on the ring may form a ring, or a pharmaceutically acceptable salt thereof;

[2] a nitrogen-containing heterocyclic compound as described in the above [1] represented by the following general formula (I-A) or (I-B):

[Chem. 2]

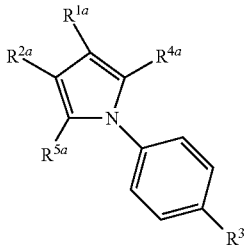

(I-A)

[Chem. 3]

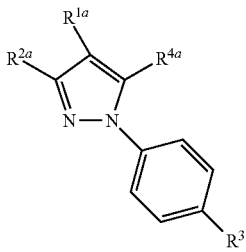

(I-B)

wherein $R^{4a}$ and $R^{5a}$ independently represent a hydrogen atom or an alkyl group;

one of $R^{1a}$ and $R^{2a}$ represents a haloalkyl group, a cyano group or a halogen atom;

the other of $R^{1a}$ and $R^{2a}$ represents an aryl group which may have a substituent selected from the group consisting of an alkyl group, a haloalkyl group, an alkoxy group and a halogen atom in which some of the substituents may form a ring, an alkoxy group or a heterocyclic group selected from the group consisting of a thienyl, thiazolyl or pyrrolyl group which may be substituted by an alkyl group or a halogen atom; and $R^3$ represents a 5-tetrazolyl group or a carboxy group, or a pharmaceutically acceptable salt thereof;

[3] a nitrogen-containing heterocyclic compound as described in the above [2], wherein $R^{1a}$ represents a cyano group, or a pharmaceutically acceptable salt thereof;

[4] a nitrogen-containing heterocyclic compound as described in the above [3], wherein $R^{2a}$ represents an aryl group which may have a substituent selected from the group consisting of an alkyl group, a haloalkyl group, an alkoxy group and a halogen atom in which some of the substituents may form a ring; an alkoxy group; or a thienyl group which may be substituted by an alkyl group or a halogen atom, or a pharmaceutically acceptable salt thereof;

[5] a nitrogen-containing heterocyclic compound as described in any of the above [2] to [4], wherein $R^3$ represents a carboxy group, or a pharmaceutically acceptable salt thereof;

[6] a nitrogen-containing heterocyclic compound as described in the above [1] represented by the following general formula (I-C):

[Chem. 4]

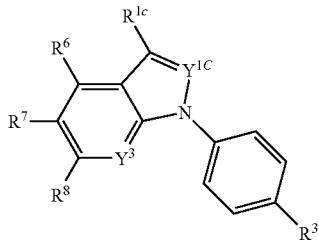

(I-C)

wherein $Y^{1C}$ represents N or $C(R^{4C})$; $Y^3$ represents N or $C(R^9)$;

$R^{4C}$ and $R^9$ independently represent an alkyl group, a haloalkyl group, a hydrogen atom, a halogen atom, a cyano group or an alkoxy group;

$R^{1C}$ represents a cyano group or a carbamoyl group;

$R^6$, $R^7$ and $R^8$ independently represent an alkyl group, a haloalkyl group, a hydrogen atom, a halogen atom, a cyano group or an alkoxy group; or any of $R^6$, $R^7$ and $R^8$ may form a ring together with the neighboring substituent; and $R^3$ represents a 5-tetrazolyl group or a carboxy group, or a pharmaceutically acceptable salt thereof;

[7] a nitrogen-containing heterocyclic compound as described in the above 6, wherein $R^{1C}$ represents a cyano group, or a pharmaceutically acceptable salt thereof;

[8] a nitrogen-containing heterocyclic compound as described in the above [6] or [7], wherein $R^3$ represents a carboxy group, or a pharmaceutically acceptable salt thereof;

[9] a pharmaceutical composition comprising a nitrogen-containing heterocyclic compound as described in any of the above [1] to [8] or a pharmaceutically acceptable salt thereof as an active ingredient;

[10] a pharmaceutical composition as described in the above [9], which is a xanthine oxidase inhibitor;

[11] a pharmaceutical composition as described in the above [9] or [10], which is an uricosuric agent;

[12] a pharmaceutical composition as described in any of the above [9] to [11], which is an agent for the treatment of gout or hyperuricemia;

[13] a pharmaceutical composition as described in the above [9], which is an agent for the treatment of ischemic-reperfusion disorder, inflammatory disease, diabetes, cancer, arteriosclerosis or neurological disease; and the like.

Furthermore, another pharmaceutical composition of the present invention is characterized in comprising as an active ingredient the above nitrogen-containing heterocyclic compound of the present invention or a pharmaceutically acceptable salt thereof.

Definitions of substituents or the like used in the present specification are as follows. The term "aryl group" means a phenyl group, a naphthyl group, a biphenyl group or the like. The term "alkyl group" may be a straight-chained, branched or cyclic one, and the number of carbon atoms is not limited but preferably 1 to 12. An alkyl part of "alkoxy group" may be a straight-chained, branched or cyclic one, and the number of carbon atoms is not limited but preferably 1 to 12 similarly to the above alkyl group.

The term "halogen atom" means a fluorine atom, a chlorine atom, a bromine atom or a iodine atom. The term "haloalkyl group" means the above alkyl group substituted by one or more (preferably 1 to 3) halogen atoms as defined above. In case that there are two or more halogen atoms, they may be different.

Effect of the Invention

Nitrogen-containing heterocyclic compounds of the present invention or pharmaceutically acceptable salts thereof are compounds which have a X.O. inhibitory effect and an uricosuric effect. Pharmaceutical compositions of the present invention comprising these compounds as an active ingredient can be expected to be useful as an agent for the treatment of gout or hyperuricemia and for the treatment of various diseases such as ischemic-reperfusion disorder, inflammatory disease, diabetes, cancer, arteriosclerosis, neurological disease or the like.

DETAIL DESCRIPTION OF THE INVENTION

In case that a nitrogen-containing heterocyclic compound represented by the general formula (I) of the present invention is a nitrogen-containing heterocyclic compound represented by the above general formula (I-A) or (I-B), one of $R^1$ and $R^2$ is preferably a cyano group, and the other of $R^1$ and $R^2$ is preferably an aryl group which may have a substituent selected from the group consisting of an alkyl group, a haloalkyl group, an alkoxy group and a halogen atom in which some of the substituents may form a ring, or an alkoxy group, or a thienyl group which may be substituted by an alkyl group or a halogen atom; and $R^1$ is more preferably a cyano group. As the above aryl group, a phenyl group is more preferable. As $R^3$, a carboxy group is preferable.

In case that a nitrogen-containing heterocyclic compound represented by the general formula (I) of the present invention is a nitrogen-containing heterocyclic compound represented by the above general formula (I-C), $R^{1C}$ is preferably a cyano group. It is preferable that $Y^{1C}$ is $C(R^{4C})$ and $Y^3$ is $C(R^9)$ at the same time wherein $R^{4C}$ and $R^9$ independently are a haloalkyl group, a hydrogen atom, a cyano group or an alkoxy group. As $R^3$, a carboxy group is preferable.

In nitrogen-containing heterocyclic compounds of the present invention, a pharmaceutically acceptable salt is not limited but includes, for example, salts with hydrochloric acid, sulfuric acid, phosphoric acid, nitric acid, acetic acid, propionic acid, succinic acid, glycolic acid, lactic acid, malic acid, oxalic acid, tartaric acid, citric acid, maleic acid, fumaric acid, methanesulfonic acid, benzenesulfonic acid, p-toluenesulfonic acid, ascorbic acid and the like. Such a salt may be a hydrate, solvate or the like.

A pharmaceutical composition of the present invention is characterized in comprising as an active ingredient a nitrogen-containing heterocyclic compound or a pharmaceutically acceptable salt thereof. The pharmaceutical compositions of the present invention are suitable as a xanthine oxidase inhibitor and/or an uricosuric agent and useful for the treatment of gout or hyperuricemia.

In addition, since xanthine oxidase is focused as an enzyme related to active oxygen generation, the pharmaceutical compositions of the present invention are expected as an agent for the treatment of diseases associated with active oxygen generation such as ischemic-reperfusion injury, inflammatory disease, diabetes, cancer, arteriosclerosis, neurological disease or the like.

In the pharmaceutical compositions of the present invention, any dosage forms can be optionally employed without limitation. For example, orally administration forms such as tablets, capsules, granules, fine granules, powders or liquids, or parenteral administration forms such as injections, topical products or suppositories can be illustrated, and they can be formulated in the usual way.

When the pharmaceutical compositions of the present invention are employed as a therapeutic agent for gout or hyperuricemia, or a disease such as ischemic-reperfusion injury, inflammatory disease, diabetes, cancer, arteriosclerosis, neurological disease, the dosage used is approximately within the range from 1 mg to 1 g for adults per day depending on the age, sex, body weight and degree of symptoms of each patient, and the daily dose can be divided into several doses.

The present invention is further illustrated by way of the following Examples. In explaining the Examples, tentative names such as "XO-TT53" are used.

EXAMPLE 1

1. Synthesis of Pyrazole Derivatives

A hydrazone, XO-TT462, was prepared by condensation reaction of acetophenone as a starting material and 4-hydrazinobenzoic acid. And then, after XO-TT462 was converted into the methyl ester, XO-TT466 was prepared by cyclization by Vilsmeier reaction and formylation. Finally, the end objective XO-TT469 was prepared by cyanation followed by ester hydrolysis in 17% total yields over 5 steps (the following scheme).

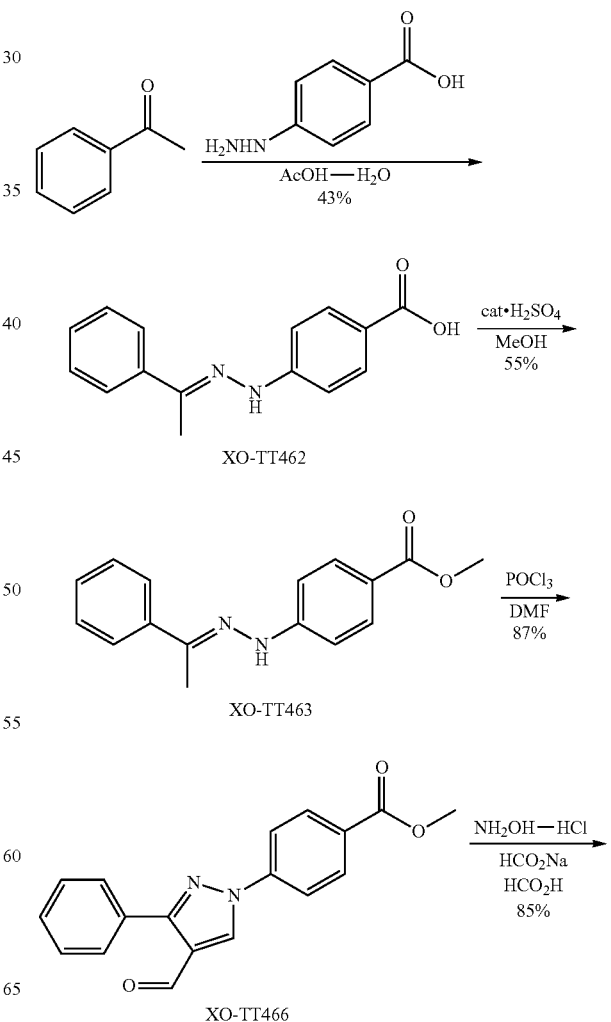

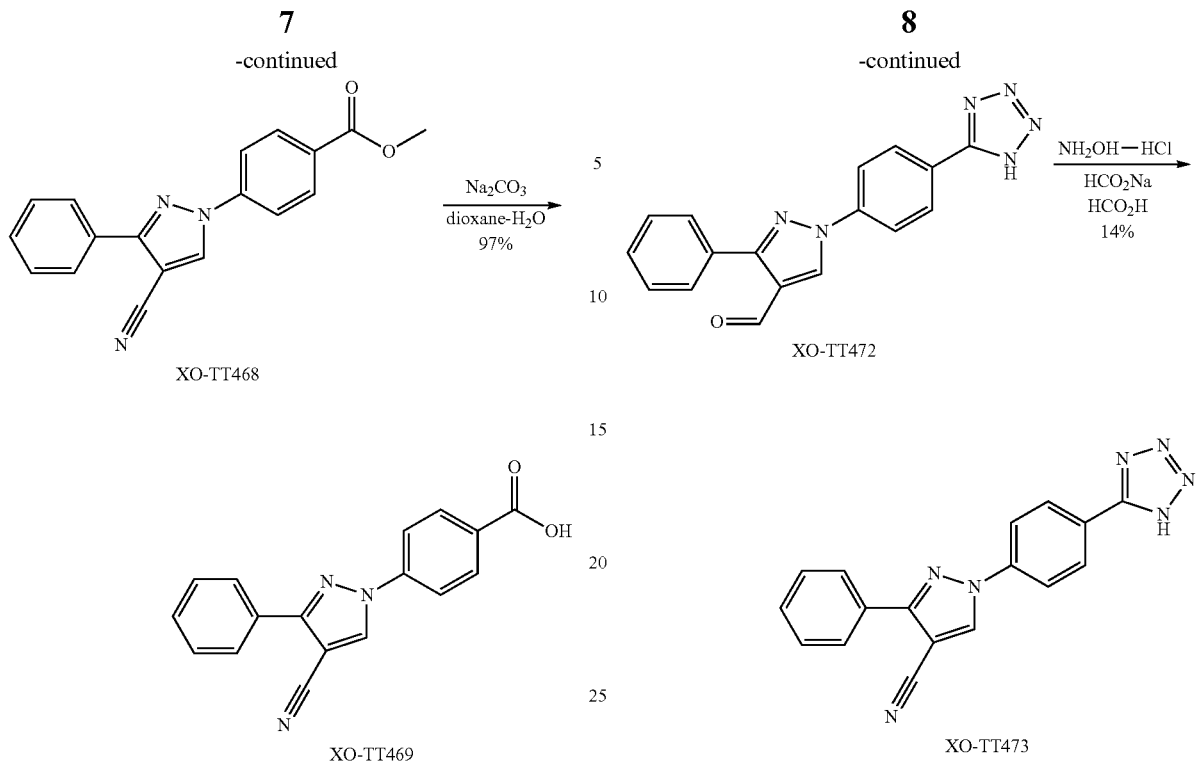

A compound wherein the carboxylic acid of XO-TT469 was converted by a tetrazole group was synthesized. The synthesis was basically the same as that for the above XO-TT466. However, in the last cyanation of XO-TT472, the reaction was conducted without protecting the tetrazole group and XO-TT473 was able to be prepared in a low yield (the following scheme).

A compound wherein a methyl group was introduced into the 5-position of the pyrazole ring of XO-TT469 was synthesized. A pyrazole, XO-TT485, was prepare by condensation reaction of 1-phenyl-1,3-butanedione and hydrazine. And a 4-phenyl-carboxylic acid unit was introduced (the following scheme).

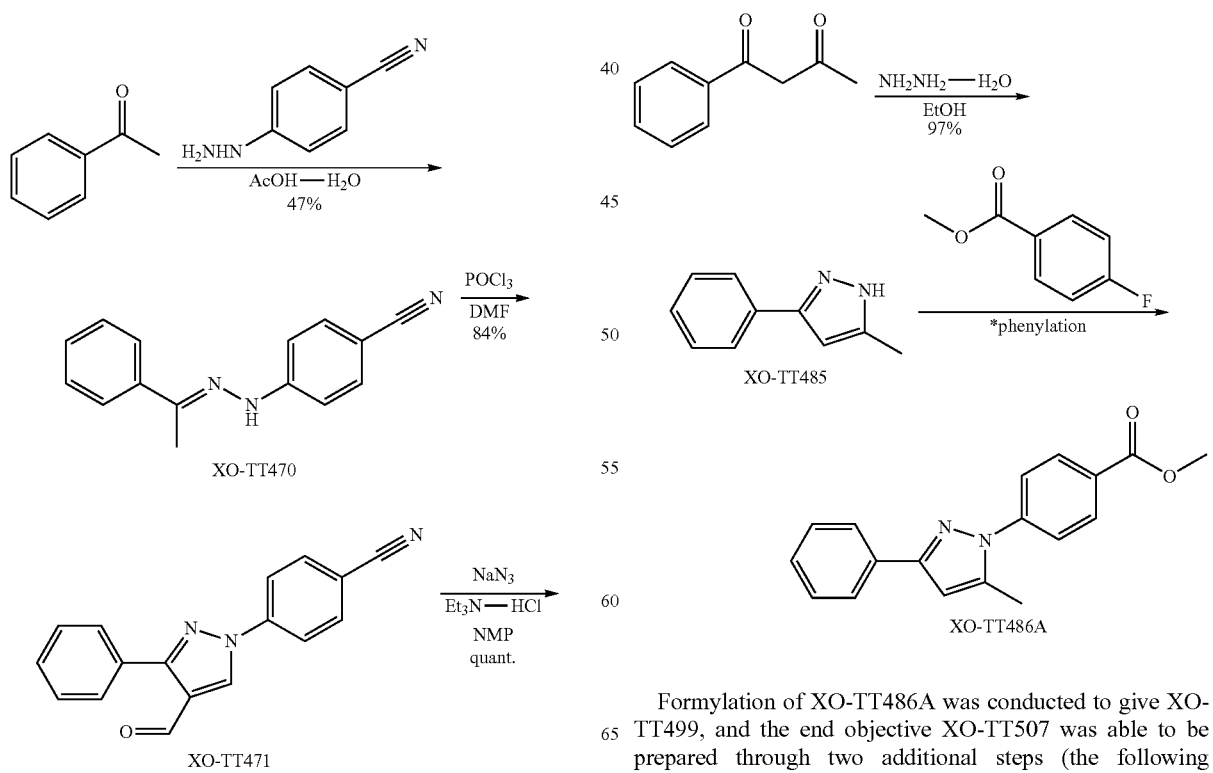

Formylation of XO-TT486A was conducted to give XO-TT499, and the end objective XO-TT507 was able to be prepared through two additional steps (the following scheme).

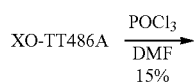

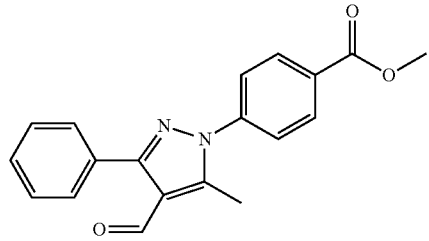

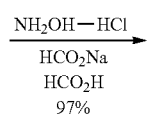

XO-TT499

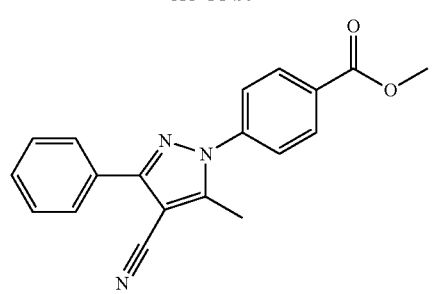

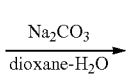

XO-TT505

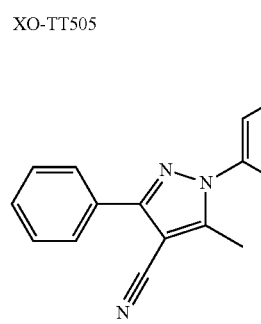

XO-TT507

A derivative wherein the terminal benzene of XO-TT469 was converted into thiophene was synthesized. First, XO-TT500 was prepared by condensation reaction of 2-acetylthiophene and 4-hydrazinobenzoic acid with ethyl esterification. And the end objective XO-TT508 was prepared in the usual way (the following scheme).

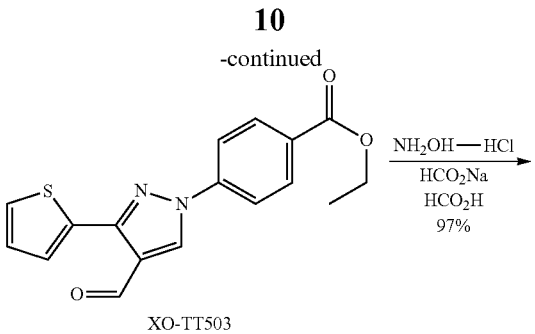

XO-TT503

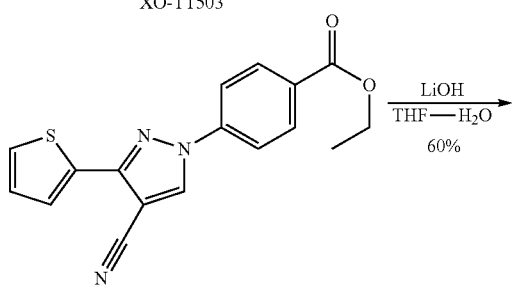

XO-TT504

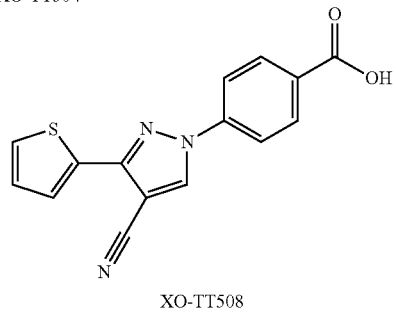

XO-TT508

2. Shortening of XO-TT469-Type Synthetic Method

An objective carboxylic hydrazone, XO-TT520, was prepared by condensation reaction of 2'-chloroacetophenone and 4-phenylcarboxylic acid unit under a condition of 2 mol/L hydrochloric acid:ethanol=1:5. And Vilsmeier reaction was conducted without protecting the carboxylic acid. As a result, XO-TT522 wherein a pyrazole ring was formed and formylated was able to be prepared. And the end objective XO-TT524 was able to be prepared by cyanation (the following scheme).

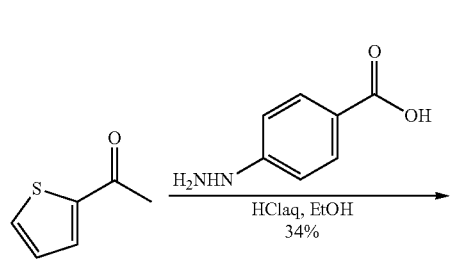

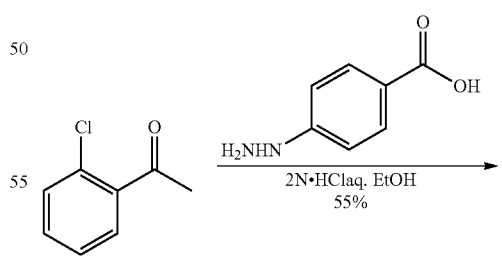

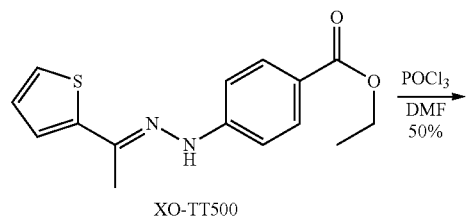

XO-TT500

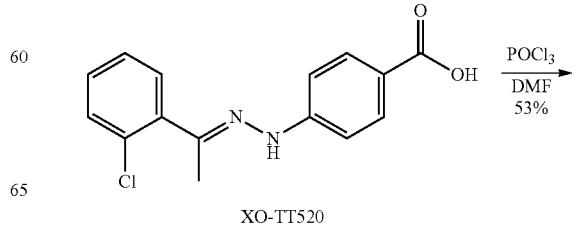

XO-TT520

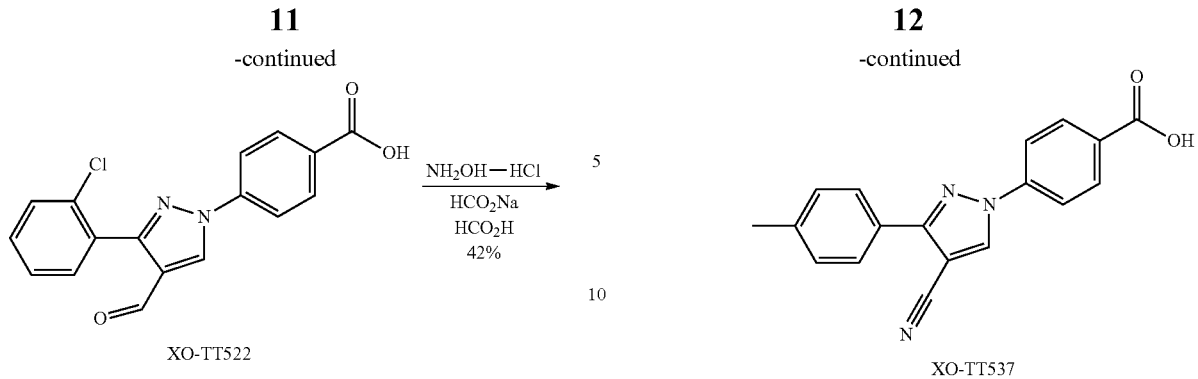

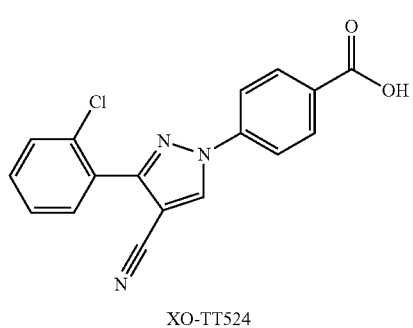

An objective carboxylic hydrazone, XO-TT534, was able to be prepared by allowing 4'-methylacetophenone to react in only ethanol as a solvent. And then the end objective XO-TT537 was prepared in the usual way (the following scheme).

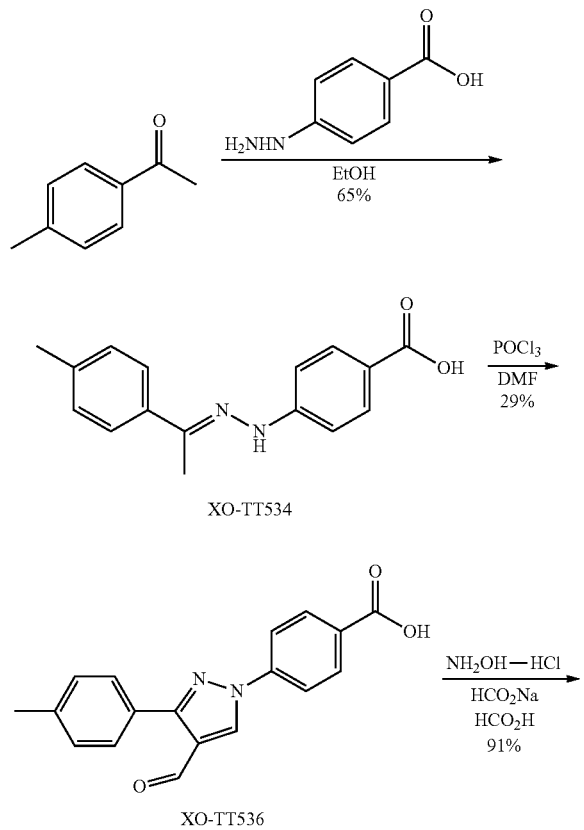

The above synthesis 1 is further illustrated in detail as follows.

XO-TT-462

To acetophenone (1.00 g, 8.32 mmol) were added acetic acid (20 mL) and water (2 mL), and to the mixture stirred was added 4-hydrazinobenzoic acid (1.27 g, 8.32 mmol). The resulting mixture was stirred at 100° C. for 21 hours. To the reaction mixture was added water (200 mL), and the solid precipitated by stirring the mixture was collected by filtration and dried in vacuo at 80° C. to give XO-TT462 as a brown solid (900 mg, 43% yield).

XO-TT463

XO-TT462 (800 mg, 3.15 mmol) was dissolved in methanol (100 mL), and to the solution was added concentrated sulfuric acid (1 mL) and the mixture was heated for reflux for 30 hours. To the reaction mixture was added water, and the mixture was extracted with ethyl acetate. The organic layer was dried over anhydrous sodium sulfate and the solvent was evaporated. The residue was purified by column chromatography on silica gel (hexane:ethyl acetate=5:1-3:1) to give XO-TT463 as a pale yellow solid (465 mg, 55% yield).

XO-TT466

A mixture of phosphorus oxychloride (0.400 mL) and dimethylformamide (3 mL) was stirred under a nitrogen atmosphere at 0° C. for 30 minutes. To the reaction mixture was added XO-TT463 (460 mg, 1.72 mmol), and the mixture was stirred at room temperature for 12 hours. To the reaction mixture was added water (200 mL), and the solid precipitated by stirring the mixture was collected by filtration and dried in vacuo at 80° C. to give XO-TT466 as a pale yellow solid (456 mg, 87% yield).

XO-TT468

To XO-TT466 (400 mg, 1.31 mmol) were added formic acid (5.0 mL), sodium formate (177 mg, 2.61 mmol) and hydroxyamine hydrochloride (109 mg, 1.57 mmol), and the mixture was heated for reflux under a nitrogen atmosphere for 45 minutes. To the reaction mixture was added water (150 mL), and the mixture was stirred and extracted with ethylacetate (200 mL). The organic layer was dried over anhydrous sodium sulfate, and the solvent was removed under reduced pressure. The residue was purified by column chromatography on silica gel (hexane:ethyl acetate =5:1 to 3:1) to give XO-TT468 as a pale yellow solid (338 mg, 85% yield).

XO-TT469

XO-TT468 (330 mg, 1.09 mmol) was dissolved in 1,4-dioxane (20 mL), and to the solution were added sodium carbonate (577 mg, 5.45 mmol) and water (5 mL). The mixture was stirred at 80° C. To the reaction mixture were added water (150 mL), 2 mol/L hydrochloric acid (30 mL), and the mixture was stirred. The precipitated solid was collected by filtration and dried in vacuo to give XO-TT469 as a white solid (306 mg, 97% yield).

XO-TT485

1-phenyl-1,3-butanedione (2.00 g, 12.3 mmol) was dissolved in ethanol, and to the solution was added hydrazine monohydrate (1.80 mL, 37.0 mmol), and the mixture was stirred at 80° C. for 3 hours. After about 80% of ethanol in the reaction solution was removed under reduced pressure, water (200 mL) was added to the residue. The precipitated solid was collected by filtration and dried in vacuo at 80° C. to give XO-TT485 as a white solid (1.88 g, 97% yield).

XO-TT486A

XO-TT485 (300 mg, 1.90 mmol) was dissolved in dimethyl sulfoxide (10 mL), and to the solution were added 40% potassium fluoride-alumina (600 mg), methyl 4-fluorobenzoate (492 mL, 3.80 mmol) and 18-crown-6 (100 mg, 0.380 mmol). The mixture was stirred at 120° C. for 2 days. To the reaction mixture was added water, and the mixture was extracted with ethyl acetate. The residue was purified by column chromatography on silica gel (hexane:ethyl acetate=10:1 to 5:1) to give XO-TT486A as a white solid (64.9 mg, 12% yield).

XO-TT500

2-acetylthiophene (1.00 g, 7.93 mmol) was dissolved in ethanol (30 mL), and to the solution were added 4-hydrazinobenzoic acid (1.21 g, 7.93 mmol) and 5 mol/L hydrochloric acid (2 mL). The mixture was stirred at 100° C. for 23 hours. To the reaction mixture was added water (200 mL), and the mixture was extracted with ethyl acetate (200 mL). The solvent was removed under reduced pressure, and the residue was purified by column chromatography on silica gel (hexane:ethyl acetate=4:1) to give XO-TT500 as a pale yellow solid (781 mg, 34% yield).

EXAMPLE 2

1. Synthesis of XO-B327

After a pyrrole compound, XO-B315, was prepared by allowing α-cyanocinnamic acid to react with tosylmethylisocyanide (88% yield), XO-B321 was prepared by coupling reaction of methyl 4-fluoro benzoate and XO-B315 (41% yield). And then, the end objective XO-B327 was synthesized by ester hydrolysis (94% yield, the following scheme).

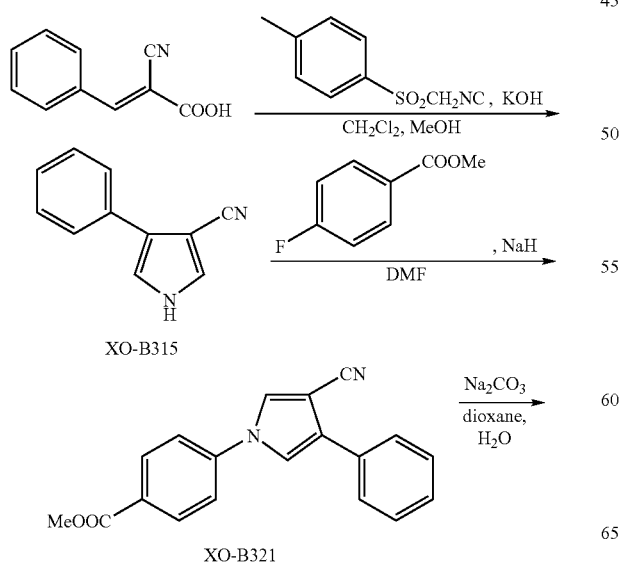

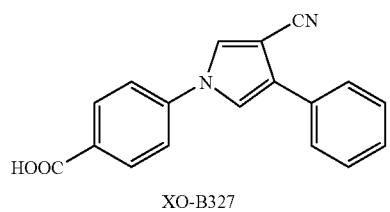

2. Synthesis of XO-B366

After XO-B348 was prepared by diazonating toluizine and by allowing it to react with ethyl benzoylacetate acid (quantitative yield), a triazole compound, XO-B351, was prepared using copper (I) iodide (89% yield). And then, XO-B358 was prepared by converting the ethoxycarbonyl group into amide (92% yield) and by dehydrating to convert it into a cyano group (88% yield). And then, a mixture of bromide compounds, XO-B362 (5% yield) and XO-B362-2 (8% yield), was prepared by brominating the methyl group, and the end objective XO-B366 was synthesized by direct hydrolysis (19% yield, the following scheme).

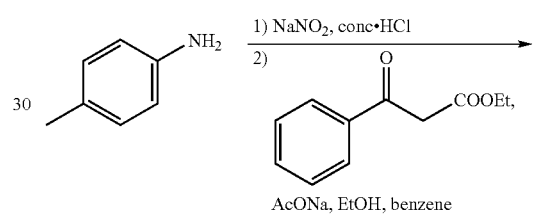

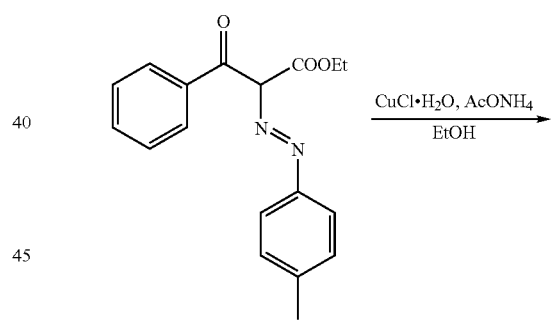

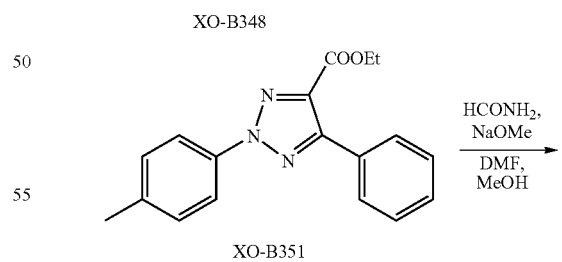

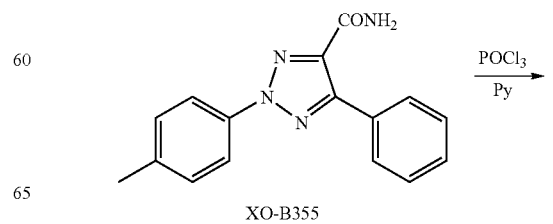

-continued

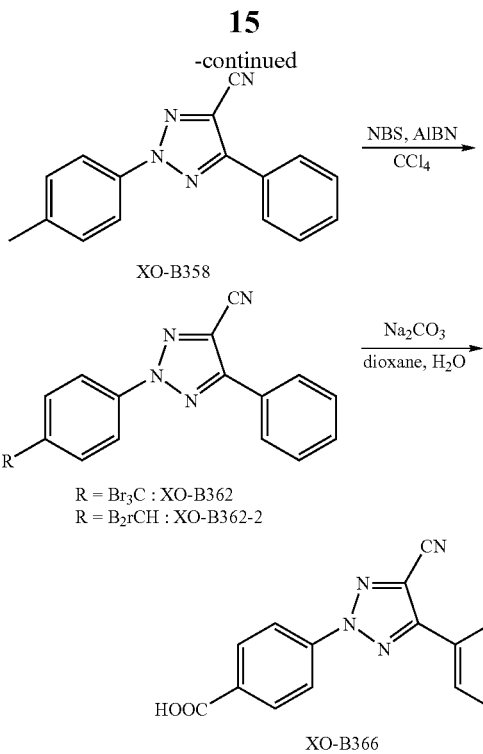

The above synthesis is further illustrated in detail as follows.

1) Synthesis of XO-B315

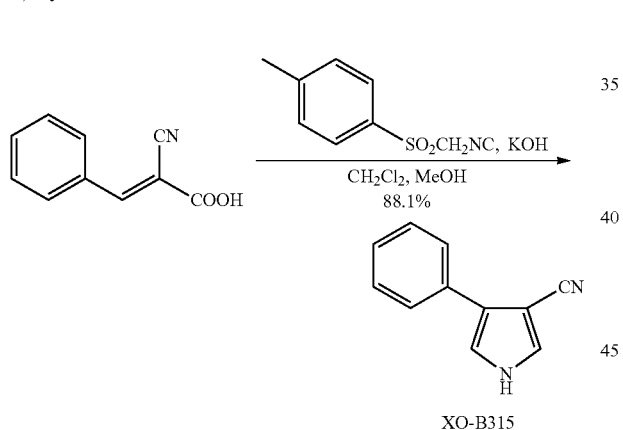

Potassium hydroxide (2.96 g, 45 mmol) was dissolved in methanol (30 mL), and the solution was cooled in ice. To the solution was added α-cyanocinnamic acid (1.73 g, 10 mmol), and the mixture was stirred under ice-cooling for 30 minutes. To the reaction mixture was added dropwise a solution of tosylmethyl isocyanide (2.05 g, 10.5 mmol) in dichloromethane (15 mL) for 17 minutes at 5° C. or lower, and the mixture was further stirred for an hour under ice-cooling. To the reaction mixture was added water (10 mL) to dissolve insoluble materials, and the mixture was adjusted to pH8 by adding 10% hydrochloric acid. The organic solvent was removed under reduced pressure, and to the residue was added water (20 mL), and the mixture was stirred at room temperature for 30 minutes. The formed solid was collected by filtration, washed with water and dried under reduced pressure at 60° C. to give XO-TT315 as a pale brown plate crystal (1.48 g, 88.1% yield).

EXAMPLE 3

1. Synthesis of 3-cyanoindole Derivatives with a Terminal Carboxylic Acid

A basic synthetic method of a derivative with a terminal carboxylic acid is shown in the following scheme.

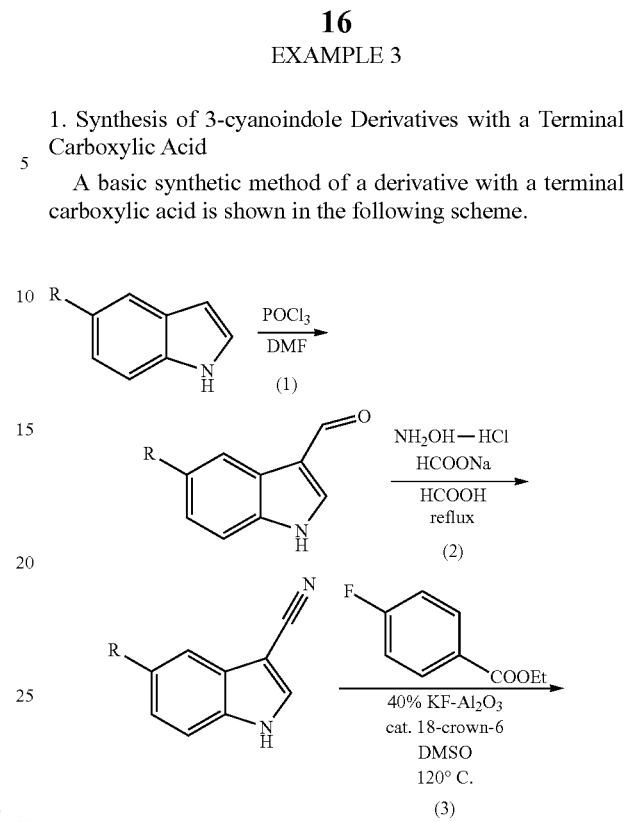

An objective compound was prepared by (1) formylation of 3-position of the corresponding indole using phosphorus oxychloride in the presence of dimethylformamide (Vilsmeier method), (2) cyanation by dehydrating reaction with hydroxylamine in sodium formate and formic acid, (3) coupling with ethyl 4-fluorobenzoate in the presence of potassium fluoride on almina and 18-crown-6-ether in dimethylsulfoxide and then, (4) hydrolysis with lithium hydroxide in total 4 steps in that order. The results are shown in the following Table 1. In addition, XO-CH146 (R=H) was prepared from the third step using 3-cyanoindole purchased.

TABLE 1

| Compound Name | R | Process | Product Name | Yield % |
|---|---|---|---|---|
| XO-CH146 | H | (3) | XO-CH144 | 60 |
|  |  | (4) | XO-CH146 | 81 |
| XO-CH160 | Cl | (1) | XO-CH154 | 97 |
|  |  | (2) | XO-CH156 |  |
|  |  | (3) | XO-CH159 | 32 (2steps) |
|  |  | (4) | XO-CH160 | 85 |
| XO-CH168 | F | (1) | XO-CH157 | 95 |
|  |  | (2) | XO-CH163 | 71 |
|  |  | (3) | XO-CH167 | 55 |
|  |  | (4) | XO-CH168 | 69 |
| XO-CH164 | Me | (1) | XO-CH155 | 90 |
|  |  | (2) | XO-CH158 | 67 |
|  |  | (3) | XO-CH161 | 47 |
|  |  | (4) | XO-CH164 | 91 |

2. Synthesis of XO-CH150

XO-CH145 was prepared by coupling of indole-3-carboaldehyde and 4-fluorobenzonitrile in a similar manner to the third step of the above 1. XO-CH147 was prepared by converting XO-CH145 into a tetrazole derivative using sodium azide, followed by cyanation using hydroxylamine to give XO-CH150 (the following scheme).

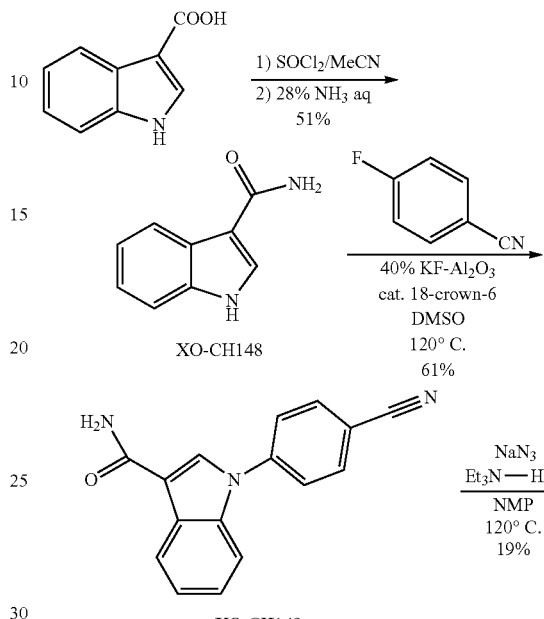

3. Synthesis of XO-CH151

XO-CH151 was prepared by converting indole-3-carboxylic acid into an acid chloride, amidating it with aqueous ammonia and then, converting to a tetrazole in a similar manner to that of XO-CH150 (the following scheme).

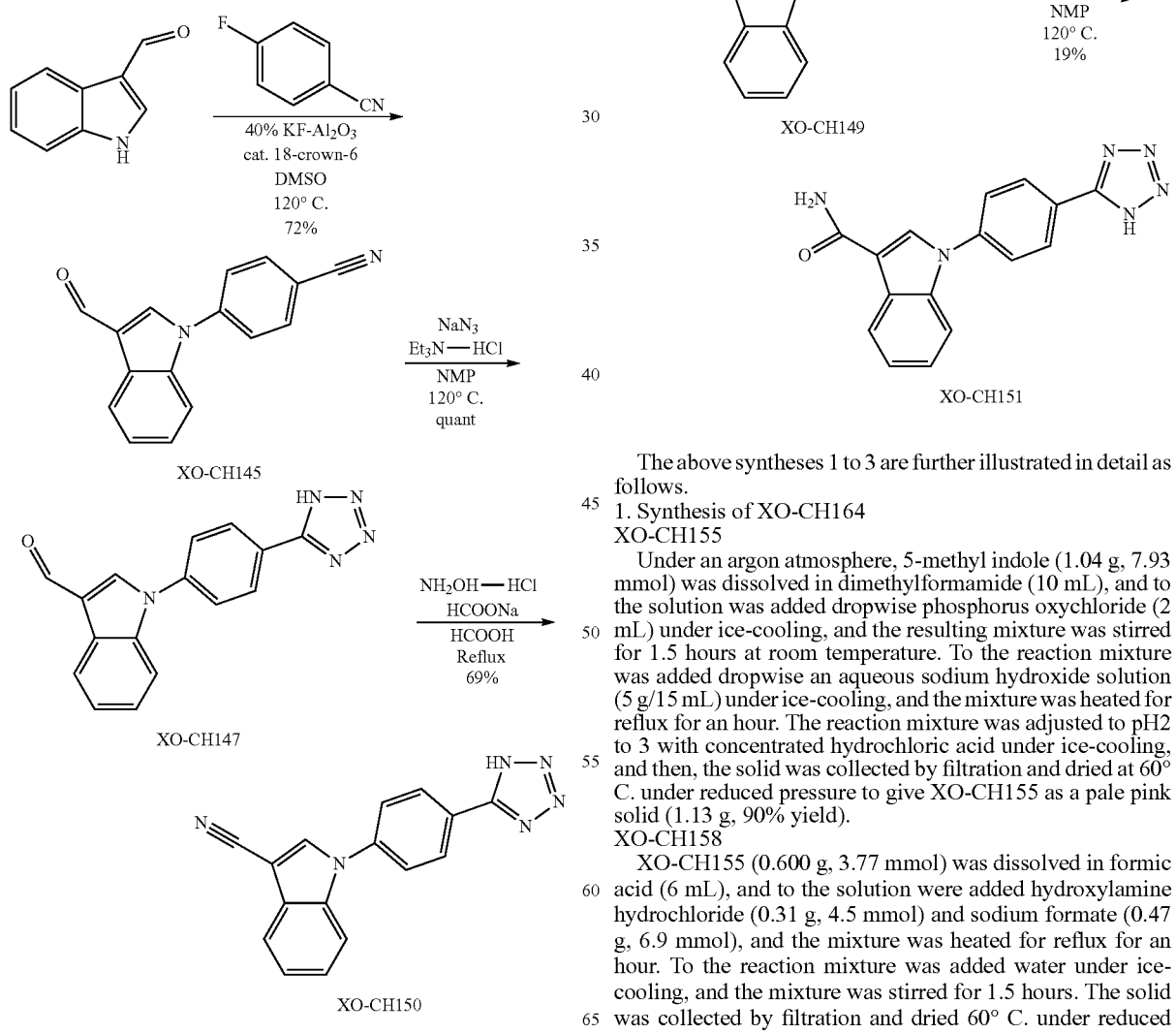

The above syntheses 1 to 3 are further illustrated in detail as follows.

1. Synthesis of XO-CH164

XO-CH155

Under an argon atmosphere, 5-methyl indole (1.04 g, 7.93 mmol) was dissolved in dimethylformamide (10 mL), and to the solution was added dropwise phosphorus oxychloride (2 mL) under ice-cooling, and the resulting mixture was stirred for 1.5 hours at room temperature. To the reaction mixture was added dropwise an aqueous sodium hydroxide solution (5 g/15 mL) under ice-cooling, and the mixture was heated for reflux for an hour. The reaction mixture was adjusted to pH2 to 3 with concentrated hydrochloric acid under ice-cooling, and then, the solid was collected by filtration and dried at 60° C. under reduced pressure to give XO-CH155 as a pale pink solid (1.13 g, 90% yield).

XO-CH158

XO-CH155 (0.600 g, 3.77 mmol) was dissolved in formic acid (6 mL), and to the solution were added hydroxylamine hydrochloride (0.31 g, 4.5 mmol) and sodium formate (0.47 g, 6.9 mmol), and the mixture was heated for reflux for an hour. To the reaction mixture was added water under ice-cooling, and the mixture was stirred for 1.5 hours. The solid was collected by filtration and dried 60° C. under reduced pressure to give XO-CH158 as a purple solid (0.397 g, 67% yield).

XO-CH161

XO-CH158 (0.387 mg, 2.48 mmol) was dissolved in dimethyl sulfoxide (20 mL), and to the solution were added ethyl 4-fluoro benzoate (0.36 mL, 2.5 mmol), 40% potassium fluoride on alumina (0.38 g) and 18-crown-6-ether (0.07 g, 0.3 mmol). The mixture was stirred at 120° C. overnight and filtered. To the filtrate was added water, and the mixture was extracted with ethyl acetate. The organic layer was washed with water (3 times) and brine, dried over anhydrous magnesium sulfate and filtered. The filtrate was concentrated and dried under reduced pressure. The residue was purified by column chromatography on silica gel (silica gel 50 g, ethylacetate/hexane=1/6) to give XO-CH161 as a white solid (0.186 g, 25% yield). In addition, the fraction containing highly-polar components obtained through the column chromatography was recrystallized with ethyl acetate/hexane to give XO-CH161 as a white solid additionally (0.165 g, 22% yield).

XO-CH164

XO-CH161 (0.186 g, 0.611 mmol) was dissolved in tetrahydrofuran (10 mL), and to the solution was added a solution of lithium hydroxide monohydrate (0.042 g, 0.99 mmol) in water (5 mL). The mixture was stirred for 6 hours at room temperature. In an ice-water bath, to the reaction mixture was added water and adjusted to pH1 with 2 mol/L hydrochloric acid. The solid was collected by filtration and dried at 60° C. under reduced pressure to give XO-CH164 as a white solid (0.154 g, 91% yield).

2. Synthesis of XO-CH146

XO-CH144

XO-CH144 was prepared in a similar manner to that of XO-CH161 as a pale brown solid (0.123 g, 60% yield).

XO-CH146

XO-CH146 was prepared in a similar manner to that of XO-CH164 as a white solid (0.082 g, 81% yield).

3. Synthesis of XO-CH160

XO-CH154

XO-CH154 was prepared in a similar manner to that of XO-CH155 as a pale yellow solid (2.34 g, 97% yield).

XO-CH156

XO-CH156 was prepared in a similar manner to that of XO-CH158 as a green-gray solid (0.96 g).

XO-CH159

XO-CH159 was prepared in a similar manner to that of XO-CH161 as a white crystal (0.57 g, 32% yield (in 2 steps)).

XO-CH160

XO-CH160 was prepared in a similar manner to that of XO-CH164 as a white solid (0.453 g, 85% yield).

4. Synthesis of XO-CH168

XO-CH157

XO-CH157 was prepared in a similar manner to that of XO-CH155 as a pale yellow solid (2.30 g, 95% yield).

XO-CH163

XO-CH163 was prepared in a similar manner to that of XO-CH158 as a green-brown solid (0.354 g, 71% yield).

XO-CH167

XO-CH167 was prepared in a similar manner to that of XO-CH161 as a pale yellow solid (0.373 g, 55% yield).

XO-CH168

XO-CH168 was prepared in a similar manner to that of XO-CH164 as a pale yellow solid (0.235 g, 69% yield).

5. Synthesis of XO-CH150

XO-CH145

XO-CH145 was prepared in a similar manner to that of XO-CH161 as a pale brown crystal (0.608 g, 72% yield).

XO-CH147

XO-CH145 (0.200 g, 0.811 mmol) was dissolved in 1-methyl-2-pyrrolidone (6 mL), and to the solution were added sodium azide (0.17 g, 2.6 mmol) and triethylamine hydrochloride (0.23 g, 1.7 mmol). The mixture was stirred for 14 hours at 120° C. To the reaction mixture was added water, and the mixture was adjusted to pH3 with 2 mol/L hydrochloric acid in an ice-water bath, and stirred for 30 minutes. The solid was collected by filtration and dried under reduced pressure at 60° C. to give XO-CH147 as a brown solid (0.248 g, quantitative yield).

XO-CH150

XO-CH150 was prepared in a similar manner to that of XO-CH158 as a red-brown solid (0.147 g, 69% yield).

6. Synthesis of XO-CH151

XO-CH148

Indole-3-carboxylic acid (0.494 g, 3.07 mmol) was suspended in dichloromethane (10 mL), and to the suspension were added thionyl chloride (0.27 mL, 3.7 mmol) and acetonitrile (5 mL). The mixture was stirred for an hour at 60° C., and to the reaction mixture was further added thionyl chloride (0.27 mL, 3.7 mmol). The mixture was stirred for an hour. After the solvent of the reaction mixture was evaporated to dryness, the residue was dissolved in acetonitrile (5 mL). To the solution was added 28% aqueous ammonia (2 mL) in an ice-water bath, and the mixture was stirred for 30 minutes. To the reaction mixture was added water, and the mixture was extracted with ethyl acetate. The organic layer was washed with water (twice) and brine and dried over anhydrous sodium sulfate and filtered. The filtrate was concentrated and dried under reduced pressure to give XO-CH148 as a pale yellow solid (0.252 g, 51% yield).

XO-CH149

XO-CH149 was prepared in a similar manner to that of XO-CH161 as a pale yellow crystal (0.102 g, 61% yield).

XO-CH151

XO-CH151 was prepared in a similar manner to that of XO-CH147 as a pale yellow solid (0.018 g, 19% yield).

EXAMPLE 4

1. Synthesis of Indole Derivatives

1) Synthesis of 3-cyanoindole Derivatives

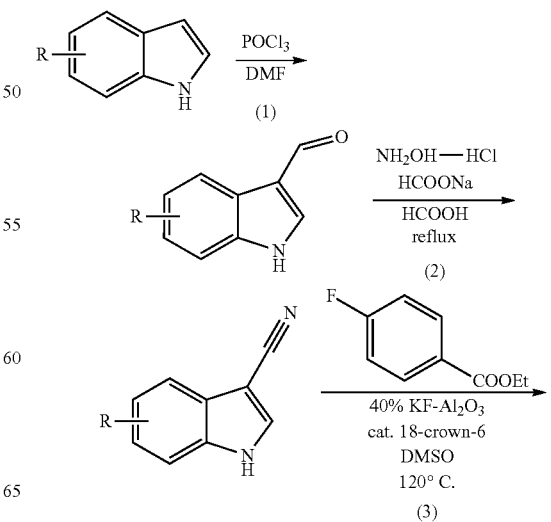

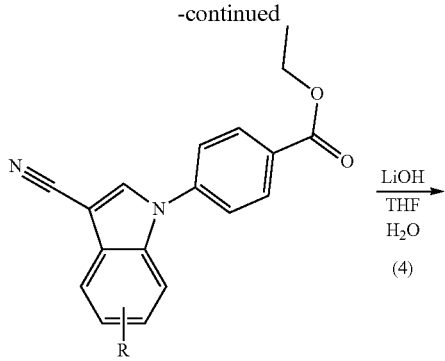

(4)

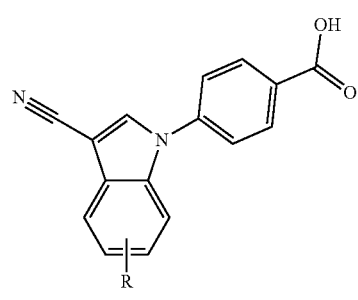

Nine objective compounds were prepared by (1) formylation of 3-position of the corresponding indole using phosphorus oxychloride in the presence of dimethylformamide (Vilsmeier 5' method), (2) cyanation by dehydrating reaction with hydroxylamine in sodium formate and formic acid, (3) coupling with ethyl 4-fluorobenzoate in the presence of potassium fluoride on almina and 18-crown-6-ether in dimethyl sulfoxide and then, (4) hydrolysis with lithium hydroxide in total 4 steps in that order (the following Table 2). In addition, XO-CH172 and XO-CH183 (R is a 2-methyl group or a 5-methoxy group, respectively) were prepared from the step (2) using the corresponding aldehydes purchased.

TABLE 2

| Compound | R | Process | Product | Yield % |
|---|---|---|---|---|
| XO-CH172 | 2-Methyl | (2) | XO-CH169 | 74 |
|  |  | (3) | XO-CH170 |  |
|  |  | (4) | XO-CH172 | 12(2steps) |
| XO-CH201 | 4-Chloro | (1) | XO-CH184 | quant. |
|  |  | (2) | XO-CH189 | 75 |
|  |  | (3) | XO-CH195 | 32 |
|  |  | (4) | XO-CH201 | 96 |
| XO-CH183 | 5-Methoxy | (2) | XO-CH171 | 69 |
|  |  | (3) | XO-CH173 | 75 |
|  |  | (4) | XO-CH183 | 79 |
| XO-CH199 | 5,6-Methylenedioxy | (1) | XO-CH178 | 92 |
|  |  | (2) | XO-CH179 | 87 |
|  |  | (3) | XO-CH190 | 52 |
|  |  | (4) | XO-CH199 | 86 |
| XO-CH200 | 6-Methyl | (1) | XO-CH180 | 94 |
|  |  | (2) | XO-CH186 | 76 |
|  |  | (3) | XO-CH192 | 60 |
|  |  | (4) | XO-CH200 | 96 |
| XO-CH207 | 6-Methoxy | (1) | XO-CH187 | 92 |
|  |  | (2) | XO-CH193 | 77 |
|  |  | (3) | XO-CH203 | 53 |
|  |  | (4) | XO-CH207 | 92 |
| XO-CH209 | 6-Chloro | (1) | XO-CH182 | 99 |
|  |  | (2) | XO-CH188 | 88 |
|  |  | (3) | XO-CH194 | 89 |
|  |  | (4) | XO-CH209 | 74 |
| XO-CH206 | 6-Trifluoromethyl | (1) | XO-CH185 | 92 |
|  |  | (2) | XO-CH191 | 82 |
|  |  | (3) | XO-CH202 | 53 |
|  |  | (4) | XO-CH206 | 88 |

TABLE 2-continued

| Compound | R | Process | Product | Yield % |
|---|---|---|---|---|
| XO-CH205 | 7-Methyl | (1) | XO-CH175 | 95 |
|  |  | (2) | XO-CH176 | 78 |
|  |  | (3) | XO-CH196 | 10 |
|  |  | (4) | XO-CH205 | 87 |

2) Synthesis of XO-CH211

An objective compound (XO-CH210) was prepared by cyanation of XO-CH208 that was prepared by formylation and coupling reaction. And then, XO-CH210 was hydrolyzed to give an objective compound (XO-CH211) (the following scheme).

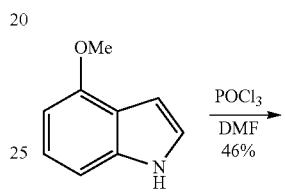

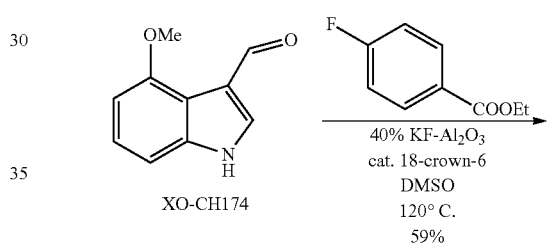

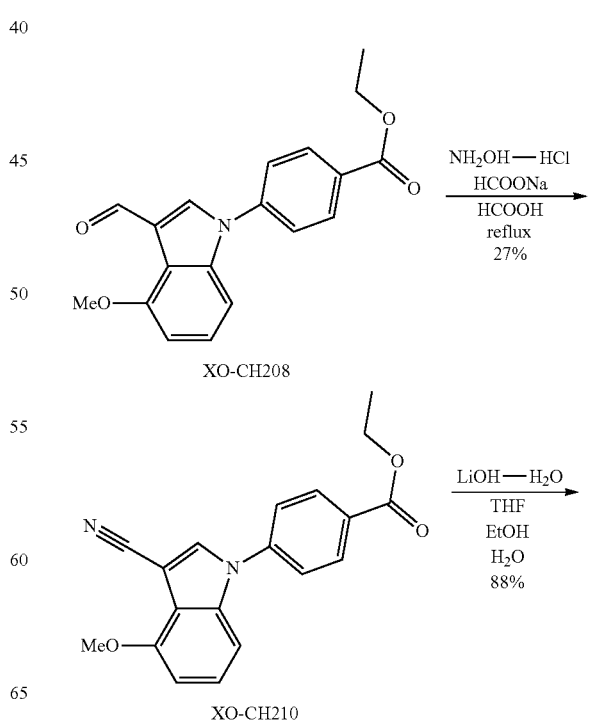

-continued

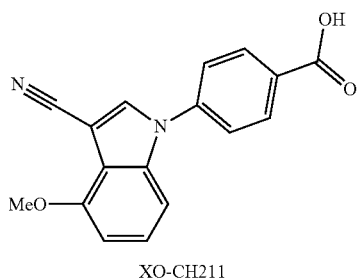

XO-CH211

2. Synthesis of 7-azaindole Derivatives

1) Synthesis of XO-KT10

XO-KT2 was prepared by coupling reaction with ethyl 4-fluorobenzoate. XO-KT5-2 was prepared by using phosphorus oxychloride with XO-KT2. Subsequently, an aldehyde of XO-KT5-2 was cyanated in the usual way, followed by hydrolysis to give XO-KT10 (the following scheme).

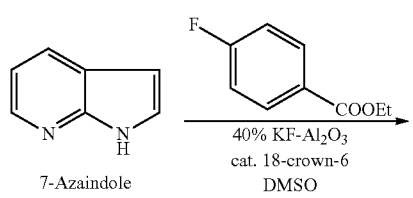

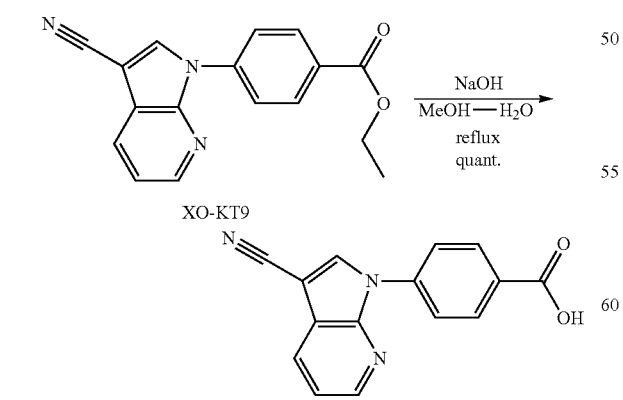

2) Synthesis of XO-KT16

A 5-bromo derivative of XO-KT10 was prepared from 5-bromo-7-azaindole in reference to the synthetic method as described in the above (1) (the following scheme).

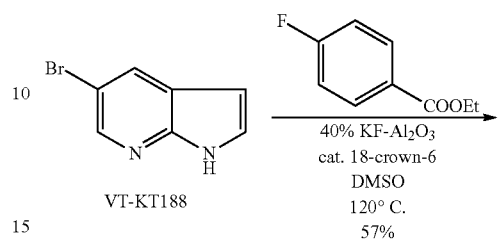

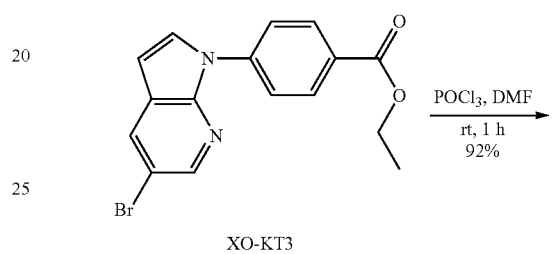

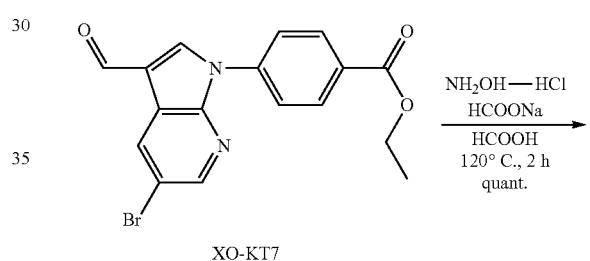

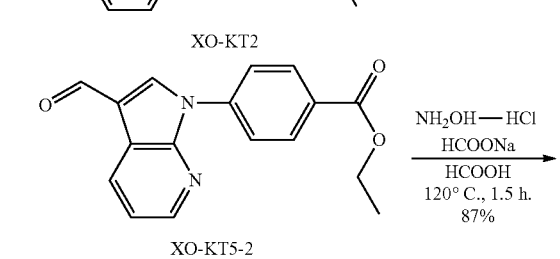

3) Synthesis of XO-KT18

Similarly, a 6-chloro derivative of XO-KT10 was prepared from 6-chloro-7-azaindole (the following scheme).

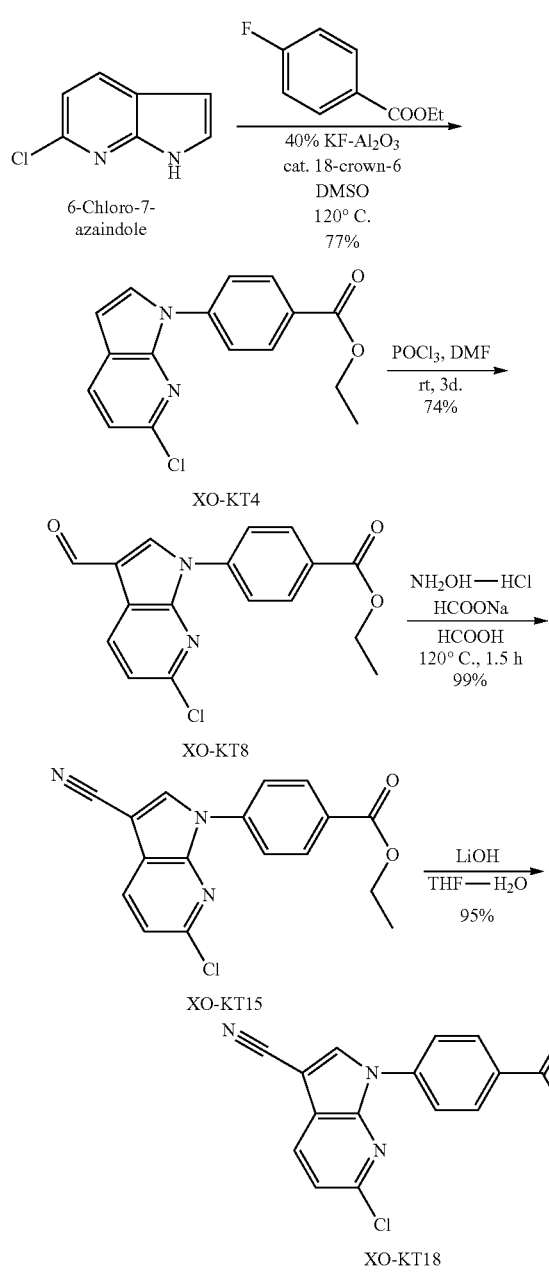

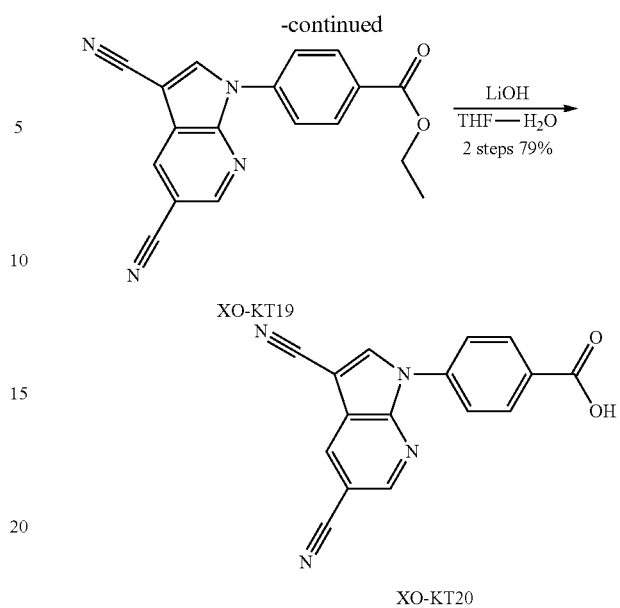

3. Synthesis of Indazole Derivatives

A iodine was introduced at 3-position of an indazole ring (the following scheme). An objective compound, XO-KT30, was prepared by converting the iodine into a cyano group using zinc cyanide, followed by coupling in the usual way, and finally by hydrolysis.

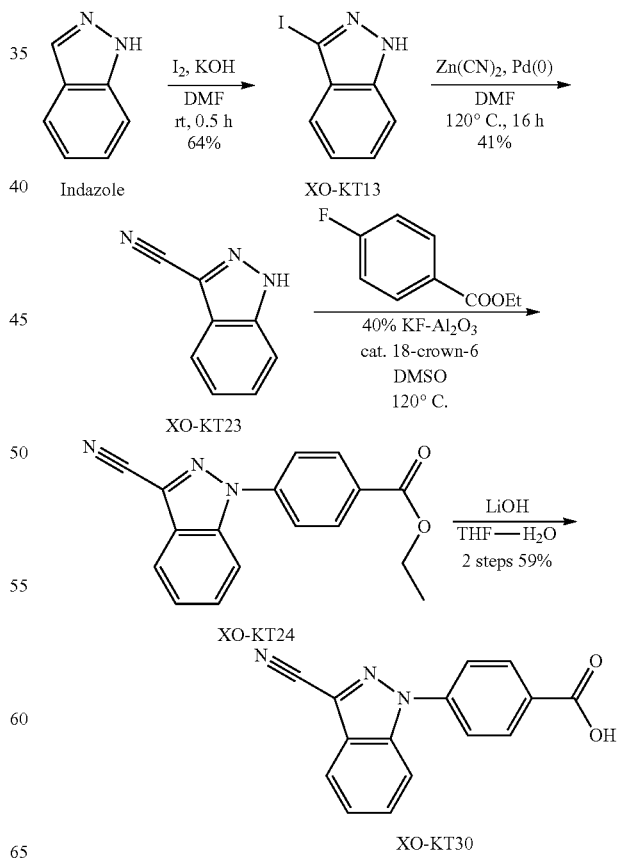

4) Synthesis of XO-KT20

A 5-cyano derivative (XO-KT20) was prepared by cyanation of XO-KT14 using zinc cyanide, followed by hydrolysis (the following scheme).

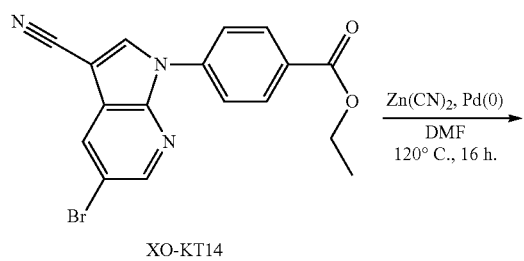

The above syntheses 1 to 3 are further illustrated in detail as follows.

1) Synthesis of XO-CH200

XO-CH180

Under an argon atmosphere, 6-methylindole (1.004 g, 7.62 mmol) was dissolved in dimethylformamide (10 mL), and to the solution was added phosphorus oxychloride (2 mL) under ice-cooling. The mixture was stirred for 1.5 hours at room temperature. To the reaction mixture was added dropwise an aqueous sodium hydroxide solution (5 g/15 mL) under ice-cooling. The mixture was heated for reflux for 1.5 hours. To the reaction mixture was added water under ice-cooling, and the mixture was adjusted to pH3 with concentrated hydrochloric acid. The solid was collected by filtration and dried at 60° C. under reduced pressure to give XO-CH180 as a pale brown solid (1.14 g, 94% yield).

XO-CH186

XO-CH180 (1.14 g, 7.16 mmol) was dissolved in formic acid (11 mL), to the solution were added hydroxylamine hydrochloride (0.63 g, 9.1 mmol) and sodium formate (0.90 g, 13 mmol). The mixture was heated for reflux for an hour. To the reaction mixture was added water under ice-cooling, and the mixture was stirred for a while. The solid was collected by filtration and dried 60° C. under reduced pressure to give XO-CH186 as a red-black solid (0.85 g, 76% yield).

XO-CH192

XO-CH186 (0.502 mg, 3.21 mmol) was dissolved in dimethyl sulfoxide (25 mL), and to the solution were added ethyl 4-fluoro benzoate (0.47 mL, 3.2 mmol), 40% potassium fluoride on alumina (0.48 g) and 18-crown-6-ether (0.10 g, 0.38 mmol). The mixture was stirred at 120° C. for 16 hours. The reaction mixture was filtered and water was added to the filtrate. The mixture was extracted with ethyl acetate (twice). The organic layer was washed with water (twice) and brine, dried over anhydrous magnesium sulfate and filtered. The filtrate was concentrated and dried under reduced pressure. The residue was purified by column chromatography on silica gel (silica gel 50 g, chloroform) to give XO-CH192 as a pale orange solid (0.589 g, 60% yield).

XO-CH200

XO-CH192 (0.298 g, 0.978 mmol) was dissolved in tetrahydrofuran, and to the solution were added an aqueous solution of lithium hydroxide monohydrate (0.0702 g, 1.67 mmol) and ethanol. The mixture was stirred for 5 hours at room temperature. In an ice-water bath, to the reaction mixture was added water, and the mixture was adjusted to pH 1 with 2 mol/L hydrochloric acid. The solid was corrected by filtration and dried at 60° C. under reduced pressure to give XO-CH200 as a pale pink solid (0.260 g, 96% yield).

2) Synthesis of XO-CH172

XO-CH169

XO-CH169 was prepared in a similar manner to that of XO-CH186 as a black-brown solid (1.45 g, 74% yield).

XO-CH170

XO-CH170 was prepared in a similar manner to that of XO-CH192 as a pale yellow solid.

XO-CH172

XO-CH172 was prepared in a similar manner to that of XO-CH200 as a pale yellow solid (0.107 g, 74% yield).

3) Synthesis of XO-CH201

XO-CH184

XO-CH184 was prepared in a similar manner to that of XO-CH180 as a pale orange solid (1.20 g, quantitative yield).

XO-CH189

XO-CH189 was prepared in a similar manner to that of XO-CH186 as a green-brown solid (0.805 g, 75% yield).

XO-CH195

XO-CH195 was prepared in a similar manner to that of XO-CH192 as a pale yellow-green solid (0.304 g, 32% yield).

XO-CH201

XO-CH201 was prepared in a similar manner to that of XO-CH200 as a pale yellow solid (0.261 g, 96% yield).

4) Synthesis of XO-CH183

XO-CH171

XO-CH171 was prepared in a similar manner to that of XO-CH186 as a black-brown solid (0.790 g, 69% yield).

XO-CH173

XO-CH173 was prepared in a similar manner to that of XO-CH192 as a white solid (0.689 g, 75% yield).

XO-CH183

XO-CH183 was prepared in a similar manner to that of XO-CH200 as a white crystal (0.496 g, 79% yield).

5) Synthesis of XO-CH199

XO-CH178

XO-CH178 was prepared in a similar manner to that of XO-CH180 as a pale brown solid (1.22 g, 92% yield).

XO-CH179

XO-CH179 was prepared in a similar manner to that of XO-CH186 as a black-brown solid (1.05 g, 87% yield).

XO-CH190

XO-CH190 was prepared in a similar manner to that of XO-CH192 as a white solid (0.468 g, 52% yield).

XO-CH199

XO-CH199 was prepared in a similar manner to that of XO-CH200 as a white solid (0.234 g, 86% yield).

6) Synthesis of XO-CH207

XO-CH187

XO-CH187 was prepared in a similar manner to that of XO-CH180 as a brown solid (1.22 g, 92% yield).

XO-CH193

XO-CH193 was prepared in a similar manner to that of XO-CH186 as a green-brown solid (0.413 g, 77% yield).

XO-CH203

XO-CH203 was prepared in a similar manner to that of XO-CH192 as a pale yellow solid (0.410 g, 53% yield).

XO-CH207

XO-CH207 was prepared in a similar manner to that of XO-CH200 as a pale yellow solid (0.346 g, 92% yield).

7) Synthesis of XO-CH209

XO-CH182

XO-CH182 was prepared in a similar manner to that of XO-CH180 as a pale yellow solid (1.20 g, 99% yield).

XO-CH188

XO-CH188 was prepared in a similar manner to that of XO-CH186 as a pale green solid (1.03 g, 88% yield).

XO-CH194

XO-CH194 was prepared in a similar manner to that of XO-CH192 as a pale yellow solid (0.810 g, 89% yield).

XO-CH209

XO-CH209 was prepared in a similar manner to that of XO-CH200 as a white crystal (0.206 g, 74% yield).

8) Synthesis of XO-CH206

XO-CH185

XO-CH185 was prepared in a similar manner to that of XO-CH180 as a pale yellow solid (0.268 g, 92% yield).

XO-CH191

XO-CH191 was prepared in a similar manner to that of XO-CH186 as a pale blue-green solid (0.213 g, 82% yield).

XO-CH202

XO-CH202 was prepared in a similar manner to that of XO-CH192 as a pale yellow solid (0.191 g, 53% yield).

XO-CH206

XO-CH206 was prepared in a similar manner to that of XO-CH200 as a pale yellow solid (0.155 g, 88% yield).

9) Synthesis of XO-CH205
XO-CH175
XO-CH175 was prepared in a similar manner to that of XO-CH180 as a yellow solid (1.15 g, 95% yield).
XO-CH176
XO-CH176 was prepared in a similar manner to that of XO-CH186 as a black-brown solid (0.762 g, 78% yield).
XO-CH196
XO-CH196 was prepared in a similar manner to that of XO-CH192 as a pale yellow solid (0.095 g, 10% yield).
XO-CH205
XO-CH205 was prepared in a similar manner to that of XO-CH200 as a white solid (0.075 g, 87% yield).
10) Synthesis of XO-CH211
XO-CH174
XO-CH174 was prepared in a similar manner to that of XO-CH180 as a pale pink solid (0.549 g, 46% yield).
XO-CH208
XO-CH208 was prepared in a similar manner to that of XO-CH192 as a yellow solid (0.598 g, 59% yield).
XO-CH210
XO-CH210 was prepared in a similar manner to that of XO-CH186 as a pale yellow solid (0.162 g, 27% yield).
XO-CH211
XO-CH211 was prepared in a similar manner to that of XO-CH200 as a pale yellow solid (0.130 g, 88% yield).
11) Synthesis of XO-KT1.0
XO-KT2
XO-KT2 was prepared in a similar manner to that of XO-CH192 (1.32 g, 50% yield).
XO-KT5-2
XO-KT2 (560 mg, 2.1 mmol) was dissolved in dimethylformamide (4.3 mL), and to the solution was added phosphorus oxychloride (0.8 mL). The mixture was stirred for 2 hours at room temperature. After the reaction, to the reaction mixture was added an aqueous sodium hydroxide solution (2.7 g/8 mL), and the mixture was heated for reflux for an hour. After the reaction, the reaction mixture was cooled to room temperature, and extracted with ethyl acetate and water added. The organic layer was washed with brine and dried over anhydrous magnesium sulfate, and the solvent was concentrated under reduced pressure. The residue was purified by column chromatography on silica gel (dichloromethane:methanol=5:1) to give XO-KT5-2 (374 mg, 61% yield).
XO-KT9
XO-KT9 was prepared in a similar manner to that of XO-CH186 (0.354 g, 87% yield).
XO-KT10
XO-KT2 (266 mg, 1 mmol) was dissolved in a mixed solvent of methanol (4 mL) and water (4 mL), and to the solution was added sodium hydroxide (80 mg). The mixture was heated for reflux for 0.5 hour. After the reaction, the reaction mixture was cooled to room temperature, and acetic acid (0.5 mL) was added to the reaction mixture. The precipitate was collected by filtration, washed and dried to give XO-KT6 (230 mg, 97% yield).
12) Synthesis of XO-KT16
XO-KT3
XO-KT3 was prepared in a similar manner to that of XO-CH192 (57% yield).
XO-KT7
XO-KT3 (3.45 g, 10 mmol) was dissolved in dimethylformamide (30.5 mL), and to the solution was added phosphorus oxychloride (3.8 mL). The mixture was stirred for 72 hours at room temperature. After the reaction, to the reaction mixture were added an aqueous sodium hydroxide solution (12.9 g/38 mL) slowly and then water (200 mL). The precipitate was collected by filtration, washed and dried to give XO-KT7 (3.42 g, 92% yield).
XO-KT14
XO-KT3 was prepared in a similar manner to that of XO-CH186 (quantitative yield).
XO-KT16
XO-KT16 was prepared in a similar manner to that of XO-CH200 (0.333 g, 97% yield).
13) Synthesis of XO-KT18
XO-KT4
XO-KT4 was prepared in a similar manner to that of XO-CH192 (77% yield).
XO-KT8
XO-KT8 was prepared in a similar manner to that of XO-KT7 (74% yield).
XO-KT15
XO-KT15 was prepared in a similar manner to that of XO-CH186 (99% yield).
XO-KT18
XO-KT18 was prepared in a similar manner to that of XO-CH200 (95% yield).
14) Synthesis of XO-KT20
XO-KT19
Under an argon atmosphere, XO-KT14 (0.370-g, 1 mmol) and zinc cyanide (0.235 g, 2 mmol) were dissolved in dimethylformamide (12 mL), and to the solution was added tetrakis(triphenylphosphine)palladium (0) (0.166 g, 0.1 mmol), and the mixture was stirred at 120° C. overnight. After the reaction, the reaction mixture was cooled to room temperature, the mixture was extracted with ethyl acetate and water added. The extract was washed with brine, dried over anhydrous magnesium sulfate and concentrated under reduced pressure. The residue was recrystallized from a mixed solvent of ethyl acetate and hexane to give XO-KT19 (0.281 g, 89%).
XO-KT20
XO-KT20 was prepared in a similar manner to that of XO-CH200 (79% yield).
15) Synthesis of XO-KT30
XO-KT13
Indazole (1.18 g, 10 mmol) was dissolved in dimethylformamide (6 mL), and to the solution were added iodine (2.8 g, 11 mmol) and potassium hydroxide (2.8 g, 50 mmol), and the mixture was allowed to react for 0.5 hour at room temperature. After the reaction, the reaction mixture was extracted with ethyl acetate and water added. The organic layer was washed with brine and dried over anhydrous magnesium sulfate, and the solvent was concentrated under reduced pressure. The residue was recrystallized from a mixed solvent of ethyl acetate and hexane to give XO-KT13 (1.55 g, 64% yield).
XO-KT23
XO-KT23 was prepared in a similar manner to that of XO-KT19 (41% yield).
XO-KT30
XO-KT24 was prepared in a similar manner to that of XO-KT192, and then XO-KT30 was prepared in a similar manner to that of XO-CH200 (59% yield over 2 steps).

EXAMPLE 5

A variety of objective derivatives were synthesized according to the following reaction scheme. The results of each synthetic step are shown in the following Table 3.

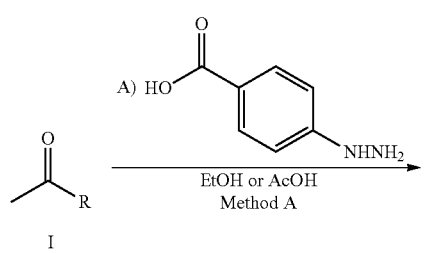
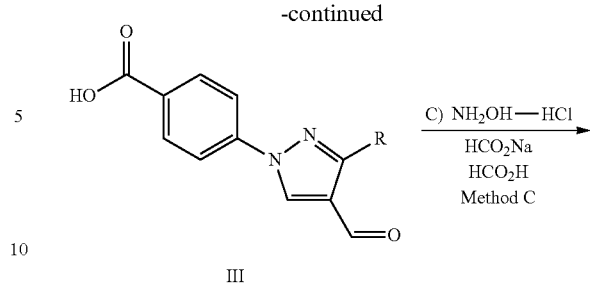
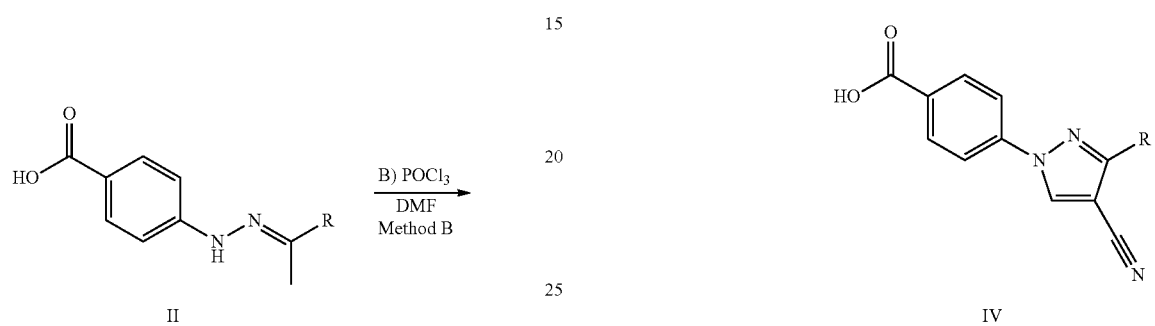
TABLE 3
| I | Method A | II | Method B | III | Method C | IV |
|---|---|---|---|---|---|---|
| 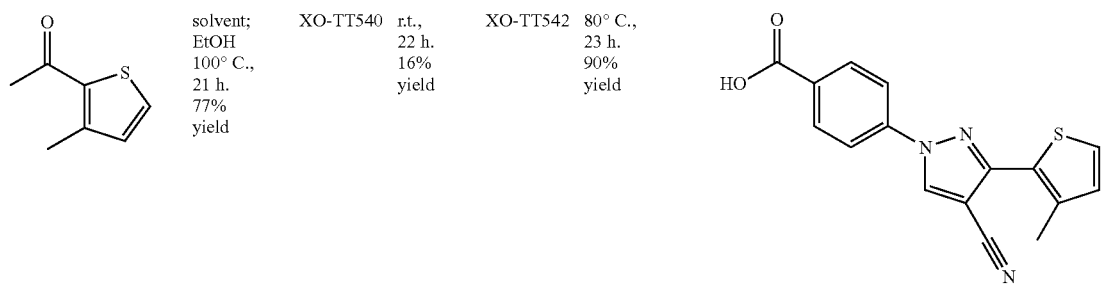 | solvent; EtOH 100° C., 46 h. 67% yield | XO-TT538 | r.t., 21 h. 57% yield | XO-TT539 | 80° C., 32 h. 59% yield | XO-TT544 |
|  | solvent; EtOH 100° C., 21 h. 77% yield | XO-TT540 | r.t., 22 h. 16% yield | XO-TT542 | 80° C., 23 h. 90% yield | XO-TT545 |

TABLE 3-continued
| I | Method A | II | Method B | III | Method C | IV |
|---|---|---|---|---|---|---|
| 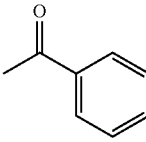 | solvent; EtOH 90° C., 21 h. 91% yield | XO-TT547 | r.t., 110 min. 23% yield | XO-TT549 | 80° C., 43 h. 69% yield | 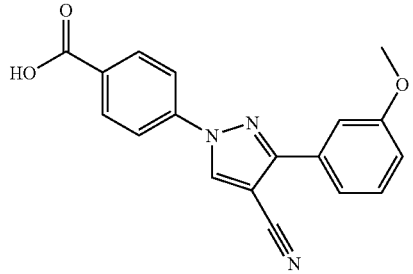<br>XO-TT552 |
| 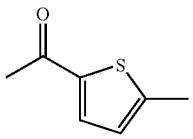 | solvent; EtOH 90° C., 23 h. 93% yield | XO-TT548 | r.t., 18 h. 56% yield | XO-TT543 | 80° C., 29 h. 92% yield | 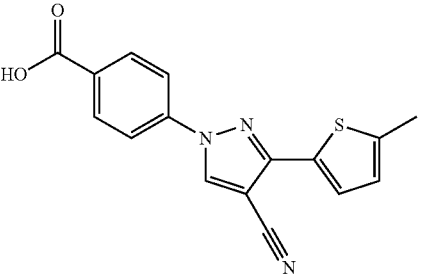<br>XO-TT554 |
| 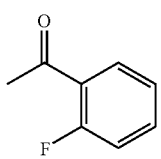 | solvent; EtOH 90° C., 23 h. 93% yield | XO-TT551 | r.t., 20 h. 58% yield | XO-TT555 | 80° C., 22 h. 92% yield | 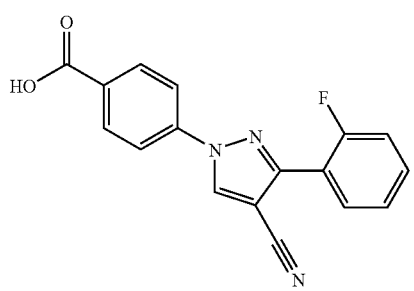<br>XO-TT559 |
| 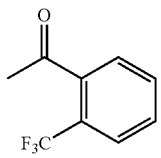 | solvent; EtOH 80° C., 22.5 h. 50% yield | XO-TT556 | r.t., 18 h. 16% yield | XO-TT558 | 80° C., 20 h. 74% yield | 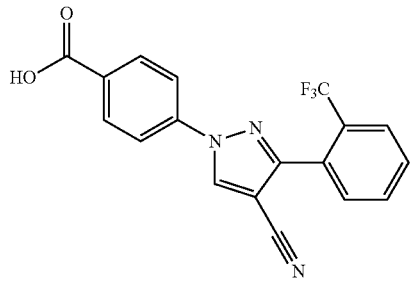<br>XO-TT561 |

TABLE 3-continued

| I | Method A | II | Method B | III | Method C | IV |
|---|---|---|---|---|---|---|
| 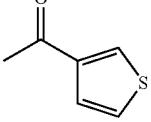 | solvent; AcOH 90° C., 27 h. 80% yield | XO-TT562 | r.t., 18 h. 75% yield | XO-TT567 | 80° C., 17 h. 94% yield | 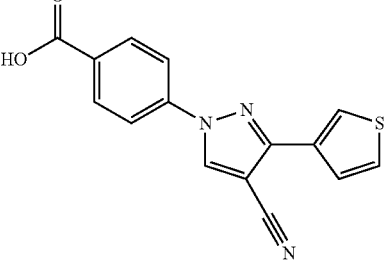<br>XO-TT571 |
| 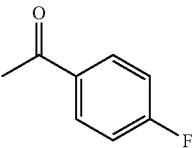 | solvent; EtOH 80° C., 18 h. 85% yield | XO-TT565 | r.t., 18 h. 53% yield | XO-TT568 | 80° C., 17 h. 82% yield | 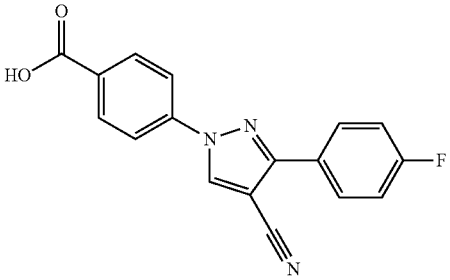<br>XO-TT572 |
| 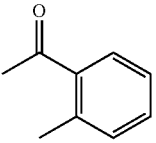 | solvent; EtOH 80° C., 18 h. 78% yield | XO-TT557 | r.t., EZmixture 14 h. 36% yield | XO-TT569 | 80° C., 17 h. 96% yield | 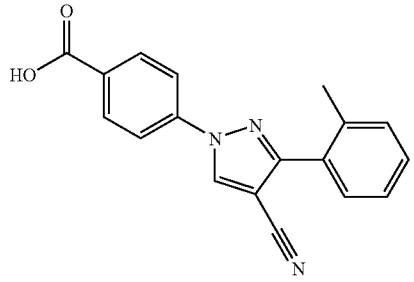<br>XO-TT573 |
| 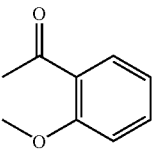 | solvent; EtOH 80° C., 16 h. 85% yield | XO-TT570 | r.t., EZmixture 17.5 h. 28% yield | XO-TT570 | 80° C., 17 h. 56% yield | 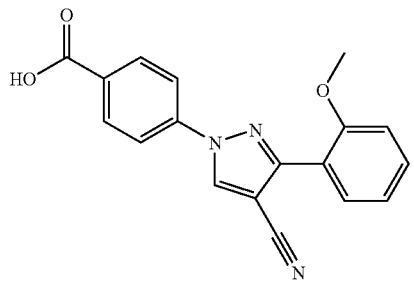<br>XO-TT574 |

The above synthesis is further illustrated in detail as follows.

XO-TT538

4'-Methoxyacetophenone (1.00 g, 6.66 mmol) was dissolved in ethanol (20 mL), and to the solution was added 4-hydrazino-benzoic acid (1.06 g, 6.99 mmol). The mixture was stirred at 100° C. for 46 hours. To the reaction mixture was added water (250 mL), and the mixture was extracted with ethylacetate (200 mL, twice). The organic layer was dried over anhydrous sodium hydroxide, and the solvent was evaporated under reduced pressure. The residue was recrystallized from acetone-water to give XO-TT538 as a pale yellow solid (1.26 g, 67% yield).

XO-TT539

A mixture of phosphorus oxychloride (0.988 mL) and dimethylformamide (10 mL) was stirred for, 30 minutes at 0° C.

under a nitrogen atmosphere. To the reaction mixture was added XO-TT538 (1.00 g, 3.52 mmol), and the mixture was stirred for 21 hours at room temperature. To the reaction mixture was added water (500 mL). The solid precipitated by stirring the mixture was collected by filtration and dried at 80° C. in vacuo to give XO-TT539 as a white solid (646 mg, 57% yield).

XO-TT544

To XO-TT539 (300 mg, 0.932 mmol) were added formic acid (10 mL), sodium formate (126 mg, 1.86 mmol) and hydroxyamine hydrochloride (77.8 mg, 1.12 mmol), and the mixture was stirred at 80° C. for 32 hours under a nitrogen atmosphere. To the reaction mixture was added water (100 mL). The solid precipitated by stirring the mixture was collected by filtration and recrystallized from acetone-water to give XO-TT544 as a white solid (176 mg, 59% yield).

EXAMPLE 6

1. Synthesis of α-cyanocinnamic acid ethyl ester Derivatives

An α-cyanocinnamic acid ethyl ester derivative was synthesized using an aldehyde and cyano acetic acid ethyl ester as starting materials by Knoevenagel condensation (the following scheme). The results were shown in the following Table 4.

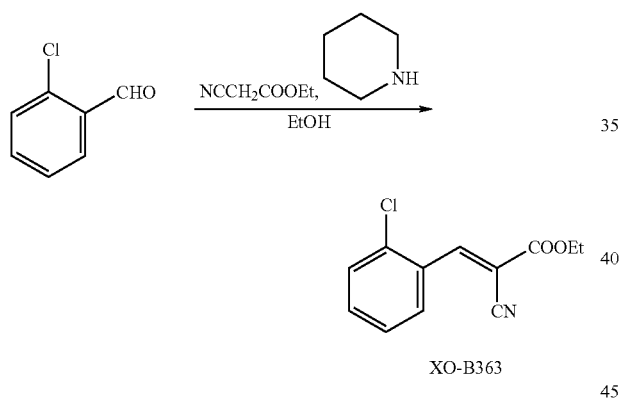

XO-B363

TABLE 4

| Compound | Yield |
| --- | --- |
| XO-B363 | 96.2% (4.53 g) |
| XO-B364 | 93.1% (3.85 g) |
| XO-B365 | 92.2% (4.26 g) |
| XO-B367 | 94.9% (4.08 g) |
| XO-B369 | 79.7% (3.45 g) |
| XO-B370 | 73.3% (3.24 g) |
| XO-B372 | 94.6% (3.86 g) |
| XO-B374 | 91.5% (4.92 g) |
| XO-B377 | 92.3% (4.46 g) |
| XO-B378 | 86.8% (3.60 g) |
| XO-B380 | 91.1% (2.25 g) |
| XO-B383 | 91.8% (4.33 g) |
| XO-B385 | 96.8% (4.47 g) |
| XO-B387 | 91.7% (3.94 g) |
| XO-B390 | 91.5% (4.92 g) |
| XO-B419 | 69.8% (3.52 g) |
| XO-B424 | 93.4% (4.09 g) |
| XO-B427 | 91.6% (4.01 g) |

In addition, the structure of each compound name listed in Table 4 is as follows.

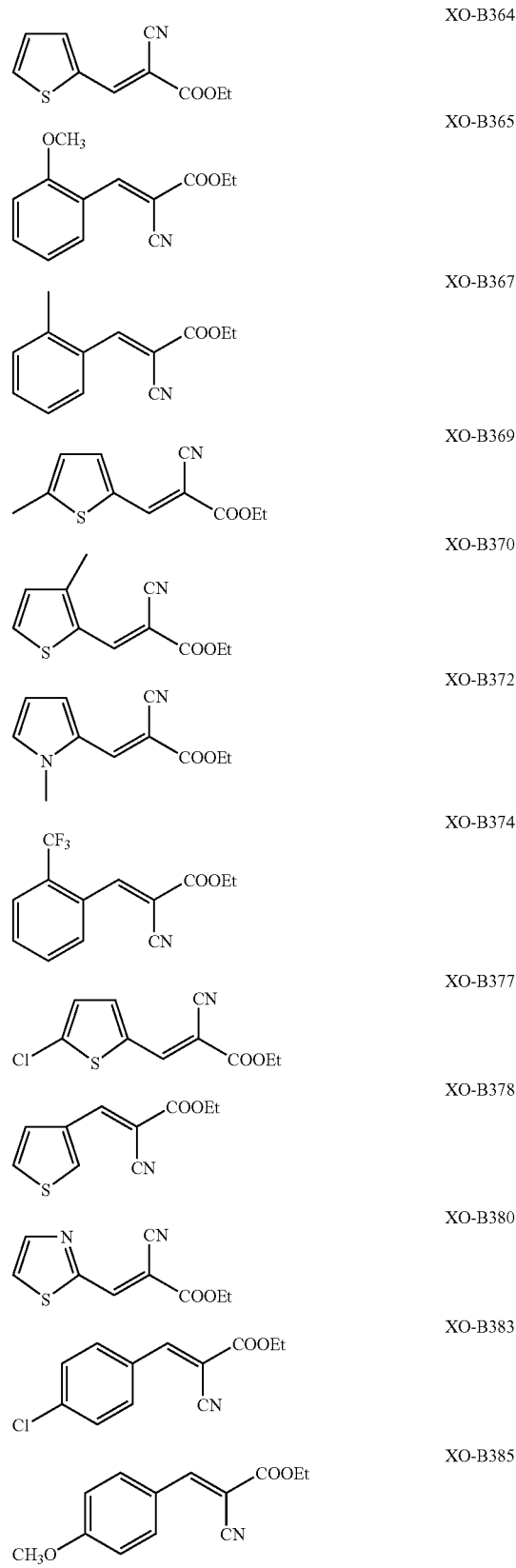

2. Synthesis of 3-cyanopyrrole Derivatives

A 3-cyanopyrrole derivative was prepared by allowing an α-cyanocinnamic acid ethyl ester derivative to react with tosylmethyl isocyanide (the following scheme). After the reaction mixture was neutralized in work-up, the organic solvent was evaporated. The solid precipitated when adding water was collected by filtration. Recrystallization was optionally conducted. In case of XO-B376, after the extraction, the solid was purified by column chromatography and recrystallization. The results were shown in the following Table 5.

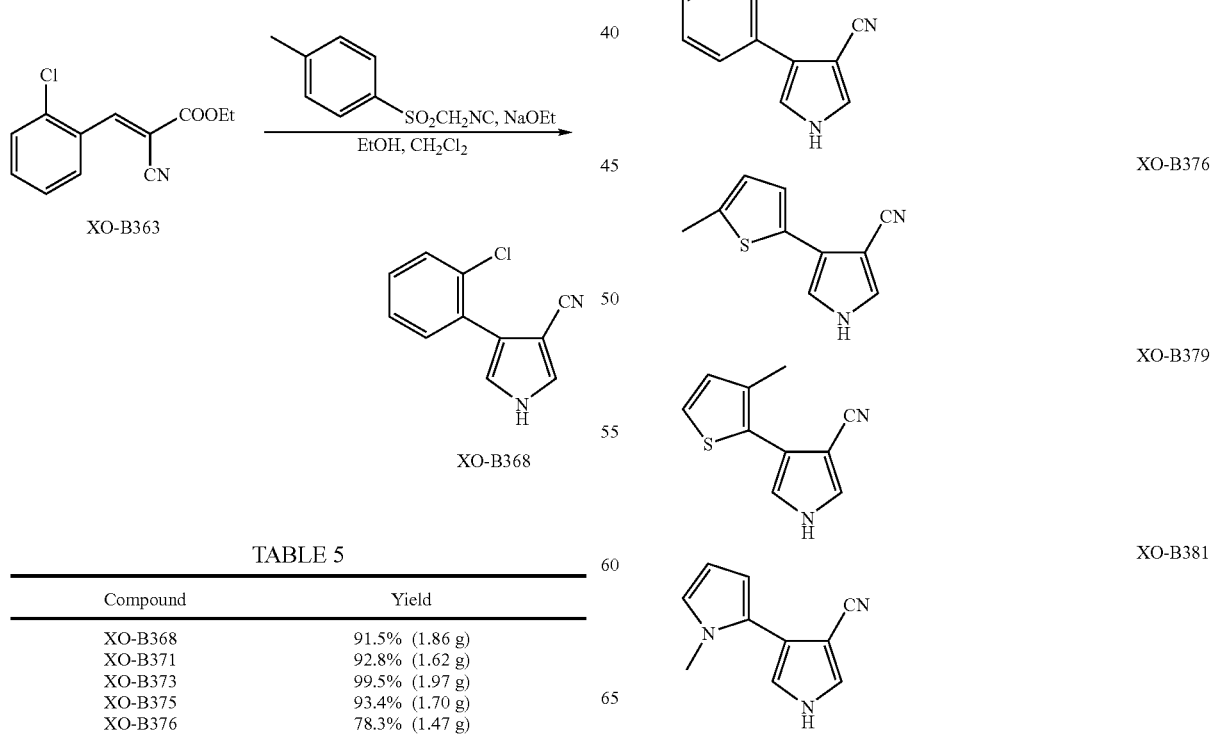

TABLE 5

| Compound | Yield |
|---|---|
| XO-B368 | 91.5% (1.86 g) |
| XO-B371 | 92.8% (1.62 g) |
| XO-B373 | 99.5% (1.97 g) |
| XO-B375 | 93.4% (1.70 g) |
| XO-B376 | 78.3% (1.47 g) |
| XO-B379 | 89.7% (1.69 g) |
| XO-B381 | 94.3% (1.61 g) |
| XO-B382 | 91.3% (2.15 g) |
| XO-B384 | 83.8% (1.75 g) |
| XO-B386 | 99.0% (1.72 g) |
| XO-B388 | 96.1% (1.68 g) |
| XO-B389 | quant. (2.08 g) |
| XO-B391 | 98.9% (1.96 g) |
| XO-B396 | quant. (1.86 g) |
| XO-B398 | quant. (2.44 g) |
| XO-B425 | quant. (2.28 g) |
| XO-B430 | 95.4% (1.77 g) |
| XO-B431 | quant. (1.88 g) |

In addition, the structure of each compound name listed in Table 5 is as follows.

XO-B382 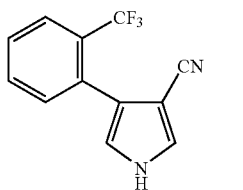

XO-B384 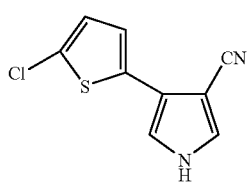

XO-B386 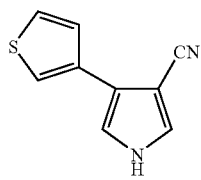

XO-B388 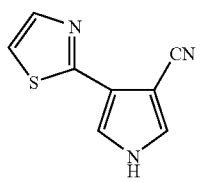

XO-B389 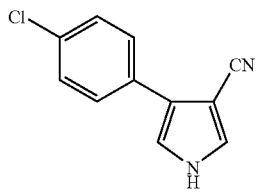

XO-B391 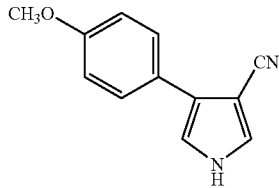

XO-B396 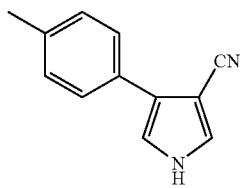

XO-B398 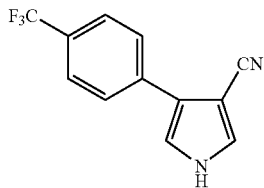

XO-B425 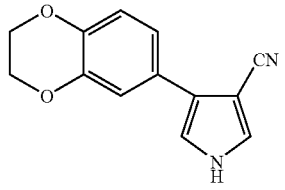

XO-B430 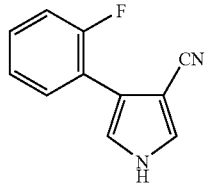

XO-B431 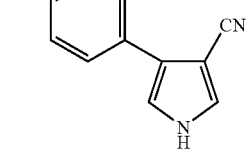

3. Synthesis of 4-(3-cyano-1-pyrroryl)benzoic acid methyl ester Derivatives

A 4-(3-cyano-1-pyrroryl)benzoic acid methyl ester derivative was synthesized by coupling of a 3-cyanopyrrole derivative and a methyl 4-fluoro benzoate (the following scheme). The reaction mixture was treated with 1 mol/L hydrochloric acid, and the precipitated solid was collected by filtration and purified by recrystallization. The results were shown in Table 6.

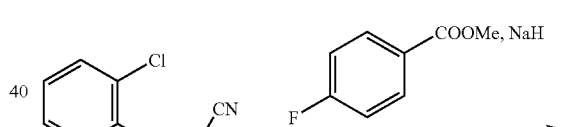

TABLE 6

| Compound | Yield |
| --- | --- |
| XO-B392 | 70.7% (1.43 g) |
| XO-B393 | 52.8% (971 mg) |
| XO-B394 | 71.9% (1.44 g) |
| XO-B395 | 57.7% (1.09 g) |
| XO-B395-1 | 7.1% (128 mg) |
| XO-B399 | 50.9% (9857 mg) |

TABLE 6-continued

| Compound | Yield |
| --- | --- |
| XO-B399-2 | 6.9% (128 mg) |
| XO-B400 | 62.4% (1.21 g) |
| XO-B402 | 60.3% (1.11 g) |
| XO-B404 | 71.0% (1.58 g) |
| XO-B406 | 70.4% (1.44 g) |
| XO-B408 | 63.9% (1.18 g) |
| XO-B409 | 67.0% (1.24 g) |
| XO-B411 | 65.1% (1.32 g) |
| XO-B413 | 73.9% (1.43 g) |
| XO-B415 | 62.1% (1.17 g) |
| XO-B416 | 52.1% (1.16 g) |
| XO-B429 | 66.6% (1.44 g) |
| XO-B432 | 70.4% (1.36 g) |
| XO-B433 | 72.9% (1.40 g) |

In addition, the structure of each compound name listed in Table 6 is as follows.

XO-B415

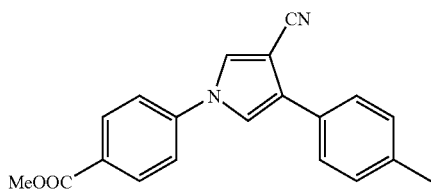

XO-B416

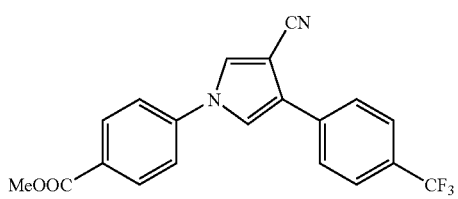

XO-B429

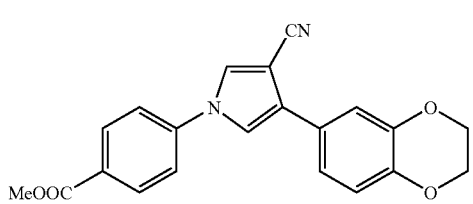

XO-B432

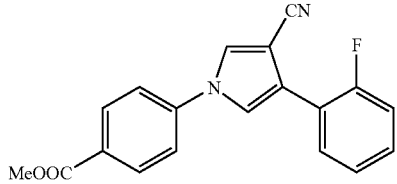

XO-B433

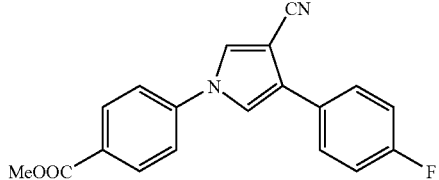

4. Synthesis of 4-(3-cyano-1-pyrroryl)benzoic acid Derivatives

An end objective 4-(3-cyano-1-pyrroryl)benzoic acid derivative was prepared by hydrolysis of the ester of a 4-(3-cyano-1-pyrroryl)benzoic acid methyl ester derivative (the following scheme). The results were shown in the following Table 7.

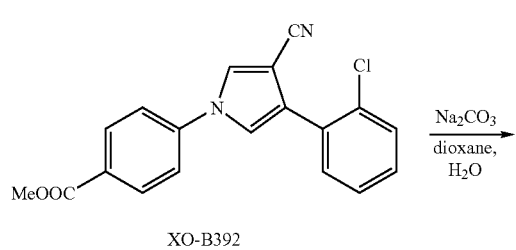

XO-B397

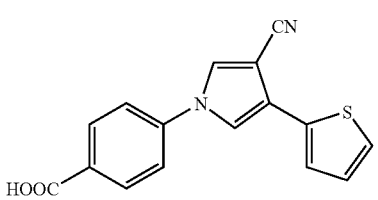

TABLE 7

| Compound | Yield |
|---|---|
| XO-B397 | 92.2% (595 mg) |
| XO-B401 | 96.2% (283 mg) |
| XO-B403 | 93.8% (298 mg) |
| XO-B395-1 | 97.6% (295 mg) |
| XO-B399-2 | 99.8% (307 mg) |
| XO-B407 | 92.4% (285 mg) |
| XO-B410 | 97.5% (284 mg) |
| XO-B412 | 95.3% (339 mg) |
| XO-B414 | 95.3% (314 mg) |
| XO-B418 | 97.8% (288 mg) |
| XO-B420 | 98.3% (290 mg) |
| XO-B421 | 98.2% (317 mg) |
| XO-B422 | 98.2% (312 mg) |
| XO-B423 | 95.8% (289 mg) |
| XO-B428 | 93.0% (331 mg) |
| XO-B434 | 98.2% (340 mg) |
| XO-B436 | 94.8% (290 mg) |
| XO-B438 | 93.9% (287 mg) |

In addition, the structure of each compound name listed in Table 7 is as follows.

XO-B401

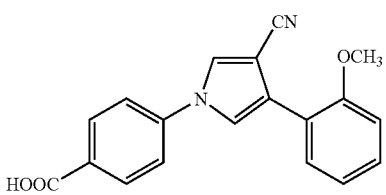

XO-B403

XO-B395-1

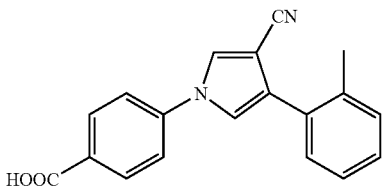

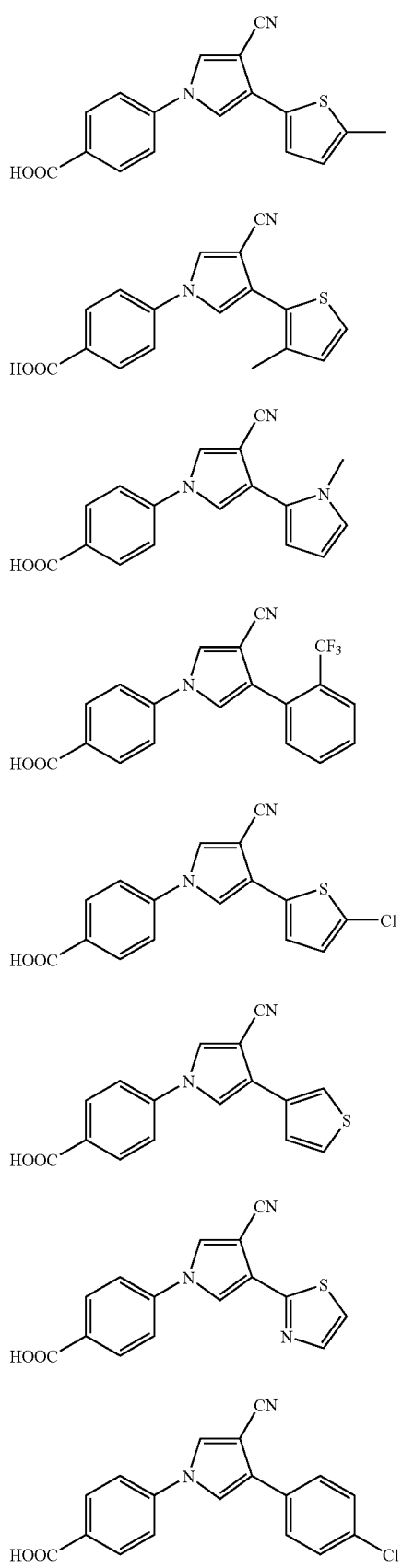
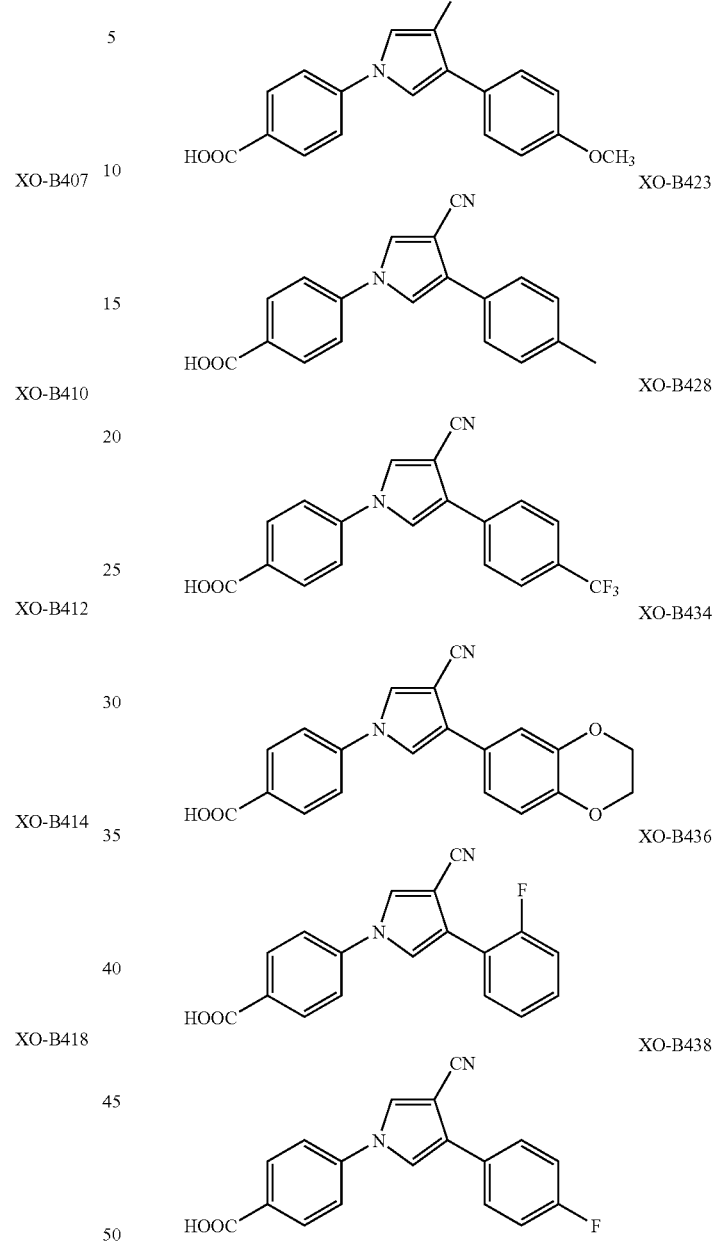
5. Synthesis of XO-B440
XO-B435 was prepared by methylation of tosylmethyl isocyanide (quantitative yield), and then, XO-B437 was synthesized by reaction to form a pyrrole (71% yield). Subsequently, an end objective XO-B446 was prepared by coupling with methyl 4-fluorobenzoate and hydrolysis of the ester of the resultant XO-B439 (42% yields over 2 steps, the following scheme).
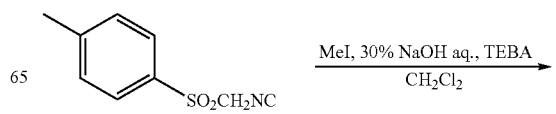

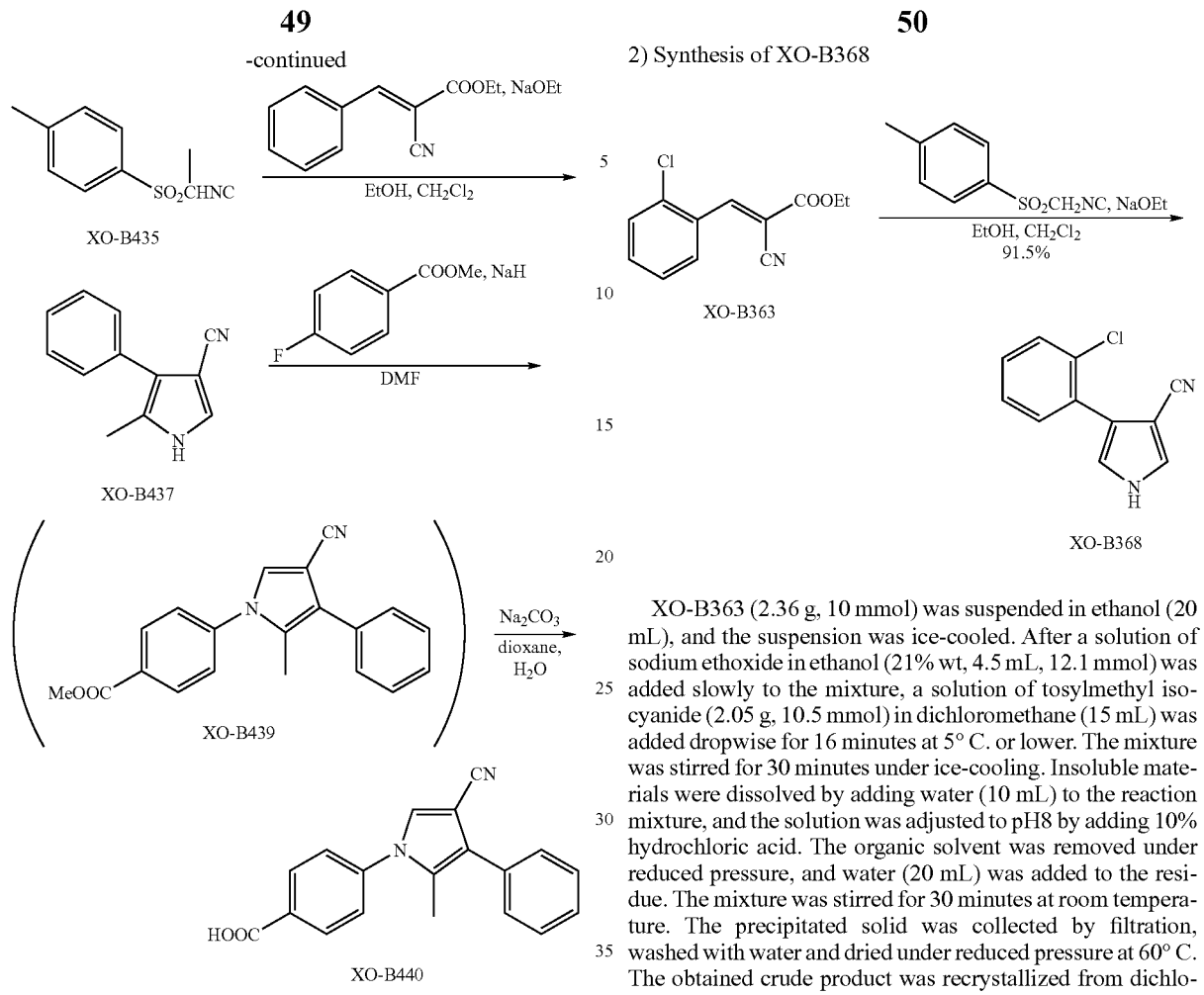

The above syntheses 1 to 5 are further illustrated in detail as follows.

1) Synthesis of XO-B363

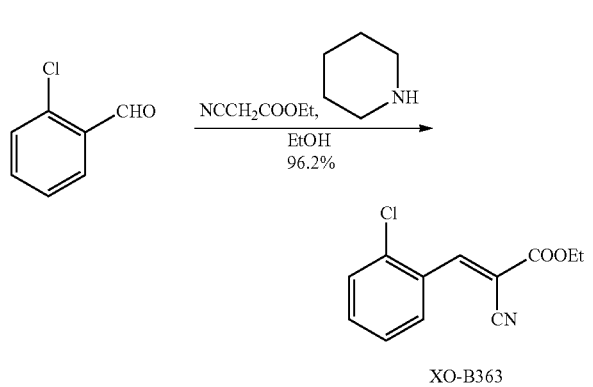

2-Chlorobenzaldehyde (2.81 g, 20 mmol) and ethyl cyanoacetate (2.26 g, 20 mmol) were mixed with ethanol (30 mL), and to the mixture was added a few drops of piperidine. The mixture was stirred for 7 hours at room temperature. The reaction mixture was concentrated under reduced pressure, and the residue was separated by column chromatography on silica gel (130 g, dichloromethane/hexane=1/1) to give XO-B363 as a white needle crystal (4.53 g, 96.24% yield).

2) Synthesis of XO-B368

XO-B363 (2.36 g, 10 mmol) was suspended in ethanol (20 mL), and the suspension was ice-cooled. After a solution of sodium ethoxide in ethanol (21% wt, 4.5 mL, 12.1 mmol) was added slowly to the mixture, a solution of tosylmethyl isocyanide (2.05 g, 10.5 mmol) in dichloromethane (15 mL) was added dropwise for 16 minutes at 5° C. or lower. The mixture was stirred for 30 minutes under ice-cooling. Insoluble materials were dissolved by adding water (10 mL) to the reaction mixture, and the solution was adjusted to pH8 by adding 10% hydrochloric acid. The organic solvent was removed under reduced pressure, and water (20 mL) was added to the residue. The mixture was stirred for 30 minutes at room temperature. The precipitated solid was collected by filtration, washed with water and dried under reduced pressure at 60° C. The obtained crude product was recrystallized from dichloromethane-hexane to give XO-B368 as a pale brown needle crystal (1.86 g, 91.51% yield).

3) Synthesis of XO-B392

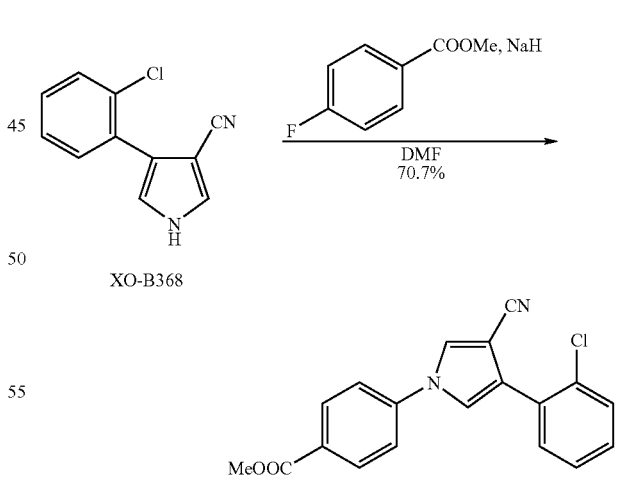

XO-B368 (1.22 g, 6 mmol) was dissolved in dimethylformamide (15 mL), and the solution was ice-cooled. After sodium hydride (55% in oil, 315 mg, 7.2 mmol) was added portionwise to the solution, methyl 4-fluorobenzoate (780 μL, 6 mmol) was added. The mixture was stirred at 150° C. for 2 hours under an argon atmosphere. After being cooled, the reaction mixture was poured into cooled 1 mol/L hydrochloric acid (45 mL). The solid precipitated was collected by filtration, washed with water and dried at 60° C. under reduced pressure. The obtained crude product was recrystallized from ethyl acetate to give XO-B392 as a pale brown needle crystal (1.43 g, 70.7% yield).

4) Synthesis of XO-B397

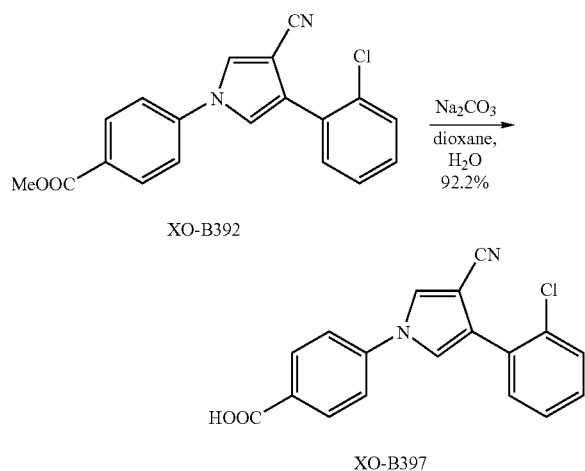

XO-B392 (637 mg, 2 mmol) was dissolved in dioxane (10 mL) with heating, and to the solution were added sodium carbonate (636 mg, 6 mmol) and water (1 mL). After the mixture was refluxed for 14 hours, dioxane (10 mL) and water (3 mL) were added to the reaction mixture. The mixture was further stirred for 72 hours. The reaction mixture was concentrated under reduced pressure. Water (30 mL) was added to the residue, and the mixture was dissolved with heating. The solution was adjusted to pH2 by adding 2 mol/L hydrochloric acid. The precipitated solid was collected by filtration, washed with water and dried at 60° C. under reduced pressure. The obtained crude product was recrystallized from tetrahydrofuran-water and dried at 60° C. under reduced pressure to give XO-B397 as a white needle crystal (595 mg, 92.2% yield).

5) Synthesis of XO-B435

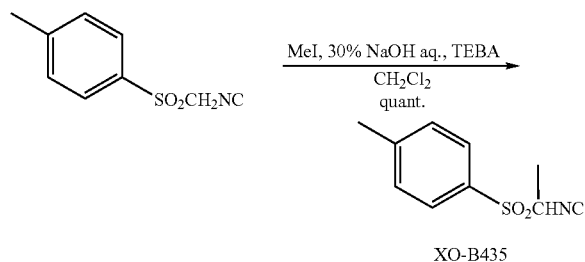

Tosylmethyl isocyanide (2.93 g, 15 mmol) was dissolved in dichloromethane (30 mL), and the solution was cooled at 0° C. To the solution were added benzyltriethylammonium chloride (683 mg, 3 mmol), methyl iodide (1.85 mL, 30 mmol) and 30% aqueous solution of sodium hydroxide (30 mL). The mixture was stirred at 0° C. for 3 hours with sealed. To the reaction mixture was added water (150 mL), and the mixture was extracted with dichloromethane (75 mL, twice). The organic layer was dried over sodium sulfate, and concentrated under reduced pressure. Since benzyltriethylammonium chloride remained, the residue was dissolved in dichloromethane (100 mL), and the solution was washed with water (30 mL, twice). The organic layer was dried over sodium sulfate and concentrated under reduced pressure to give XO-B435 as brown oil (3.26 g, quantitative yield).

The following pharmacological studies were performed with the compounds synthesized as described above.

1) Xanthine Oxidase Inhibitory Effect

Assay for inhibition of xanthine oxidase was performed in 100 μmol/L substrate concentration (final concentration), 5 mU/mL enzyme concentration (final concentration) and compounds of the present invention as test compounds which were prepared with xanthine oxidase (from buttermilk; biozyme laboratories), xanthine (Sigma) and phosphate-buffered saline (PBS). In addition, all test compounds were frozen for preservation in condition of 20 mmol/L DMSO solution and used for experiments after thawing at need. Method is following: after diluted solution of test compound was added to 90 μL of 11.1 mU/mL enzyme solution, the mixture was incubated for 10 minutes after mixing. To start reaction, 100 μL of 200 μmol/L substrate solution was added to there, 10 minutes later, the reaction was stopped by addition of 500 μL of 0.5 mol/L sulfuric acid, and then absorbance at 2.83 nm was measured. Final concentration of test compound was a single concentration, 10 μmol/L in single well for initial screening and 6 concentrations, 10, 1 μmol/L, 100, 10, 1 nmol/L, 100 pmol/L in duplicate for assay to calculate 50% inhibitory concentration ($IC_{50}$) which were used for assay. Percent inhibition was calculated according to the formula described below.

Percent inhibition (%)=$(A-B)/(A-C)\times 100$

In formula, A means absorbance in wells without test compound, B means absorbance in wells with test compound, C means absorbance in blank wells.

$IC_{50}$ value was calculated from percent inhibition in each concentration by nonlinear regression method.

2) UART1 Inhibitory Effect

DMEM containing 10% FBS (supplemented with 0.05% geneticin, Nissui Pharmaceutical Co., Ltd.), HEK293 cells forced to express URAT1 (HCS (Human cell Systems), (Fuji Biomedix)), HBSS as washing buffer and HBSS substituted with Na-gluconate (NaCl in HBSS was substituted with Na-gluconate) were used for assay. [8-$^{14}$C] uric acid (moravek) was used as an uric acid reagent and added to assay buffer at 20 μmol/L as a final concentration. Compounds of the present invention were used as a test compound, 20 mmol/L stock solution of each test compound (DMSO solution) was diluted appropriately, and then the diluted test compound solution was added to assay buffer at 100 μmol/L as a final concentration including 0.5% final concentration of DMSO.

To prepare assay plates, at first, cells on subculture petri dish were peeled off using treatment of 0.05% trypsin-EDTA solution, and then seeded on Biocoat Poly-D-Lysine Cellware 24 well plate (BECTON DICKINSON) at a density of $2\times 10^5$ cells/well and cultured for 2 days.

For the uptake study, at first, culture medium was removed by aspiration and cells were washed twice with HBSS (37° C.), then the buffer was replaced with 1 mL of assay buffer (37° C.). Cells were pre-incubated for 10 minutes. And then, the buffer was removed by aspiration and 0.5 mL of radioisotope ligand solution incubated at 37° C. was added, then cells were incubated for 5 minutes. After uptake, radioisotope solution was removed by aspiration, and immediately cells were washed three times with ice-cold HBSS, followed by resolving by addition of 0.5 mL of 0.5 mol/L NaOH. Cell lysate solution was transferred to a vial or 24 well plate for Betaplate, and mixed with 0.5 mL of liquid scintillator (Optiphase 'Super Mix'; Perkin Elmer). Radioisotope activity was measured (using Betaplate 1450). As mean count in control solution not including test compound was 100%, percent inhibition was calculated by determining percent decrease in mean count in solution including test compound from mean count in control solution.

3) Blood Hypouricemic Effect

Effect of compound of the present invention as a test compound was studied on potassium oxonate induced hyperuricemia with male 7-week-old SD rats (Charles River Japan) and potassium oxonate (Aldrich) suspended in 1% gum arabic solution. Test compound was suspended in 0.5% CMC-Na solution, and then administered orally. Dosing was 10 mg/kg or 50 mg/kg. All volume of administered solution was 10 mL/kg. Potassium oxonate 250 mg/kg was administered to dorsal region of rats subcutaneously, 1 hour later each test compound was administered orally. For control group, only 0.5% CMC-Na solution as a vehicle was administrated. At 2 hours after administration of test compounds or vehicle, blood was collected under ether anesthesia, and serum was separated according to general method. Treated number was 5 for each group.

Measurement of concentration of uric acid was conducted with following prepared reagents. The deproteinization reagent was prepared in the following manner; 100 g of sodium tungstate was added to a 2 L flask, and exactly 75 mL of 85% phosphoric acid and 500 mL of water were added to the flask equipped with a reflux condenser, and heated for an hour. After cooling, the resulting faint yellow-green solution was diluted to 1 L exactly. Sodium carbonate-urea reagent was prepared in the following manner; 14 g of anhydrous sodium carbonate and 14 g of urea were dissolved in water and final volume of the solution was adjusted to 100 mL exactly. Phosphotungstic coloring reagent was prepared in 4-fold dilution of deproteinzation reagent described above with water. UA standard solution (10 mg/dL: Kyokuto pharmaceutical industrial CO., LTD) was used as an uric acid standard solution, and then serially diluted uric acid standard solution with purified water was also used for standard curve.

Three hundred μL of serum or standard was added to 2.1 mL of purified water, and then 150 μL of deproteination reagent was also added to the solution, followed by mixing. After incubating for 20 minutes, the mixture was centrifuged at 3000 rpm for 10 minutes. Sodium carbonate-urea reagent (0.5 mL) was added to 1.5 mL of supernatant, and the mixture was incubated for 20 minutes. Next, after addition of 250 μL of coloring reagent, further incubation was carried over 15 minutes. Absorbance at 660 nm was measured, and concentration of uric acid was calculated with standard curve. Percent decrease in concentration of uric acid was calculated by following formula.

Percent decrease in concentration of uric acid (%)= $(A-B)/A \times 100$

In formula, A means average of concentration of blood uric acid in control group, B means average of concentration of blood uric acid in test compounds-treated group.

The structural formulas, NMR and MS data and the results from the pharmacological studies of the synthesized compounds of the present invention are shown in the following Tables 8 to 15.

TABLE 8

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-TT469 | | 8.18 | — | 75.0% (10 mg/kg) | 1H NMR(200 MHz) δ (DMSO-d6); 7.53-7.63 (3 H, m), 7.98-8.02 (2 H, m), 8.06 (2 H, d, J = 9.1 Hz), 8.12 (2 H, d, J = 9.1 Hz), 9.57 (1 H, s). MS(EI)m/z 289(M+). |
| XO-TT473 | | 16.0 | — | — | 1H NMR(200 MHz) δ (DMSO-d6); 7.49-7.65 (3 H, m), 7.99-8.04 (2 H, m), 8.19 (2 H, d, J = 9.0 Hz), 8.25 (2 H, d, J = 9.0 Hz), 9.58 (1 H, s). MS(EI)m/z 313 (M+), 285. |

TABLE 9

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-TT507 | | — | — | — | 1H NMR(200 MHz) δ (CDCl3); 2.62 (3 H, s), 7.45-7.50 (3 H, m), 7.67 (2 H, d, J = 8.8 Hz), 8.04 (2 H, dd, J = 2.3 Hz, 8.0 Hz), 8.29 (2 H, d, J = 8.8 Hz). MS(−ESI)m/z 302 (+ESI) 326, 304. |
| XO-TT508 | | 3.74 | 67.1 | — | 1H NMR(200 MHz) δ (DMSO-d6); 7.27 (1 H, dd, J = 4.0 Hz, 4.9 Hz), 7.77-7.79 (2 H, m), 8.02 (2 H, d, J = 8.8 Hz), 8.13 (2 H, d, J = 8.8 Hz), 9.54 (1 H, s), 12.94-13.64 (br). MS(−ESI)m/z 294 (+ESI) 318, 296. |
| XO-TT524 | | 5.18 | — | 68.7% (10 mg/kg) | 1H NMR(200 MHz) δ (DMSO-d6); 7.50-7.72 (4 H, m), 7.97 (2 H, d J = 8.5 Hz), 8.09 (2 H, d, J = 8.5 Hz), 9.55 (1 H, s). |
| XO-TT537 | | 4.86 | — | — | 1H NMR(200 MHz) δ (DMSO-d6); 2.39 (3 H, s), 7.39 (2 H, d, J = 8.2 Hz), 7.89 (2 H, d, J = 8.2 Hz), 8.07-8.15 (4 H, m), 9.54 (1 H, s). MS(−ESI)m/z 302 (+ESI) 326, 304. |
| XO-TT544 | | 3.77 | — | 71.1% (10 mg/kg) | 1H NMR(200 MHz) δ (DMSO-d6); 3.84 (3 H, s), 7.14 (2 H, d, J = 8.8 Hz), 7.94 (2 H, d, J = 8.8 Hz), 8.05 (2 H, d, J = 9.0 Hz), 8.12 (2 H, d, J = 9.0 Hz), 9.53 (1 H, s). MS(−ESI)m/z 318 (+ESI) 342, 320. |

TABLE 9-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-TT545 | | 5.21 | — | 75.8% (10 mg/kg) | 1H NMR(200 MHz) δ (DMSO-d6); 2.48 (3 H, s), 7.12 (1 H, d, J = 5.0 Hz), 7.70 (1 H, d, J = 5.0 Hz), 8.04 (2 H, d, J = 8.8 Hz), 8.13 (2 H, d, J = 8.8 Hz), 9.57 (1 H, s), 12.76-13.55 (br). MS(−ESI)m/z 308 (+ESI) 332, 310. |
| XO-TT552 | | 5.59 | — | — | 1H NMR(200 MHz) δ (DMSO-d6); 3.85 (3 H, s), 7.12 (1 H, m), 7.47-7.56 (3 H, m), 8.07 (2 H, d, J = 9.0 Hz), 8.13 (2 H, d, J = 9.0 Hz), 9.56 (1 H, s). MS(−ESI)m/z 318 (+ESI) 320. |
| XO-TT554 | | 5.44 | — | 60.5% (10 mg/kg) | 1H NMR(200 MHz) δ (DMSO-d6); 2.50 (3 H, s), 6.96 (1 H, d, J = 3.6 Hz), 7.57 (1 H, d, J = 3.6 Hz), 7.99 (2 H, d, J = 8.8 Hz), 8.12 (2 H, d, J = 8.8 Hz), 9.5 (1 H, s). MS(−ESI)m/z 308 (+ESI) 328, 310. |
| XO-TT559 | | 2.91 | — | 75.9% (10 mg/kg) | 1H NMR(200 MHz) δ (DMSO-d6); 7.38-7.51 (1 H, m), 7.58-7.69 (1 H, m), 7.80 (1 H, dt, J = 1.7 Hz, 7.6 Hz), 8.06 (2 H, d, J = 9.0 Hz), 8.13 (2 H, d, J = 9.0 Hz), 9.60 (1 H, s). MS(−ESI)m/z 306 (+ESI) 330, 308. |

TABLE 10

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-TT561 | | 8.47 | — | — | 1H NMR(200 MHz) δ (DMSO-d6); 7.72-8.16 (8 H, m), 9.60 (1 H, s), 12.88-13.37 (br). MS(−ESI)m/z 356 (+ESI) 380, 338. |
| XO-TT571 | | 4.79 | 70.8 | 62.0% (10 mg/kg) | 1H NMR(200 MHz) δ (DMSO-d6); 7.67 (1 H, dd, J = 1.3 Hz, 5.0 Hz), 7.79 (1 H, dd, J = 2.9 Hz, 5.1 Hz), 8.03-8.17 (5 H, m), 9.52 (1 H, s), 13.08-13.38 (br). MS(−ESI)m/z 294 (+ESI) 296. |
| XO-TT572 | | 4.12 | — | 56.1% (10 mg/kg) | 1H NMR(200 MHz) δ (DMSO-d6); 7.44 (2 H, dt, J = 2.0 Hz, 8.9 Hz), 7.40-7.49 (6 H, m), 9.57 (1 H, s), 12.80-13.50 (br). MS(−ESI)m/z 306 (+ESI) 308. |
| XO-TT573 | | 4.00 | — | 66.3% (10 mg/kg) | 1H NMR(200 MHz) δ (DMSO-d6); 2.43 (3 H, s), 7.36-7.46 (4 H, m), 8.04 (2 H, d, J = 9.0 Hz), 8.13 (2 H, d, J = 9.0 Hz), 9.57 (1 H, s). MS(−ESI)m/z 302 (+ESI) 304, 326. |
| XO-TT574 | | 5.52 | — | — | 1H NMR(200 MHz) δ (DMSO-d6); 3.87 (3 H, s), 7.10 (1 H, dd, J = 7.5 Hz, 8.0 Hz), 7.22 (1 H, d, J = 8.0 Hz), 7.51 (1 H, d, J = 7.5 Hz), 7.59 (1 H, dd, J = 1.7 Hz, 7.6 Hz), 8.03 (2 H, d, J = 8.7 Hz), 8.11 (2 H, d, J = 8.7 Hz), 9.49 (1 H, s). MS(−ESI)m/z 318 (+ESI) 320, 342. |

TABLE 10-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-B366 | | 77.7 | — | — | 1H NMR(200 MHz) δ (DMSO-d6); 7.44-7.57 (2 H, m), 7.78-7.88 (1 H, m), 7.97-8.07 (2 H, m), 8.17 (2 H, d, J = 9 Hz), 8.27 (2 H, d, J = 9 Hz). MS(−ESI)m/z 289.1 (M − 1+). |
| XO-B327 | | 4.90 | — | 74.1% (10 mg/kg) | 1H NMR(200 MHz) δ (DMSO-d6); 7.30-7.41 (1 H, m), 7.43-7.55 (2 H, m), 7.74 (2 H, dd, J = 1.7 Hz), 7.90 (2 H, d, J = 9 Hz), 8.08 (2 H, d, J = 9 Hz), 8.10 (1 H, d, J = 2 Hz), 8.51 (1 H, d, J = 2 Hz). MS(+ESI)m/z 289.1 (M + 1+). MS(−ESI)m/z 287.1 (M − 1+). |

TABLE 11

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-B395-1 | | 3.59 | — | 79.1% (10 mg/kg) | 1H NMR(200 MHz) δ (DMSO-d6); 2.37 (3 H, s), 7.22-7.40 (4 H, m), 7.80 (1 H, d, J = 2 Hz), 7.88 (2 H, d, J = 9 Hz), 8.07 (2 H, d, J = 9 Hz), 8.50 (1 H, d, J = 2 Hz), 13.14 (1 H, brs). MS(+ESI)m/z 303.1 (M + 1+). MS(−ESI)m/z 301.1 (M − 1+). |
| XO-B397 | | 5.24 | — | 76.7% (10 mg/kg) | 1H NMR(200 MHz) δ (DMSO-d6); 7.40-7.51 (2 H, m), 7.51-7.58 (1 H, m), 7.58-7.67 (1 H, m), 7.87 (2 H, d, J = 9 Hz), 7.90 (1 H, d, J = 2 Hz), 8.07 (2 H, d, J = 9 Hz), 8.52 (1 H, d, J = 2 Hz). MS (+ESI)m/z 323.1 (M + 1+), 325.1 (M + 2 + 1+). MS(−ESI)m/z 321.1 (M − 1+), 323.1 (M + 2 − 1+). |

TABLE 11-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-B399-2 | | 5.56 | — | 69.4% (10 mg/kg) | 1H NMR(200 MHz) δ (DMSO-d6); 6.84 (1 H, dd, J = 1, 3 Hz), 7.21 (1 H, d, J = 3 Hz), 7.86 (2 H, d, J = 9 Hz), 7.95 (1 H, d, J = 2 Hz), 8.06 (2 H, d, J = 9 Hz), 8.47 (1 H, d, J = 2 Hz), 13.13 (1 H, brs). MS(+ESI)m/z 309.1 (M + 1+). MS(−ESI)m/z 307.1 (M − 1+) |
| XO-B401 | | 5.98 | 59.5 | 78.8% (10 mg/kg) | 1H NMR(200 MHz) δ (DMSO-d6); 7.16 (1 H, dd, J = 4, 5 Hz), 7.44 (1 H, dd, J = 1, 4 Hz), 7.55 (1 H, dd, J = 1, 5 Hz), 7.88 (2 H, d, J = 9 Hz), 8.05 (1 H, d, J = 2 Hz), 8.07 (2 H, d, J = 9 Hz), 8.50 (1 H, d, J = 2 Hz), 13.16 (1 H, brs). MS(+ESI)m/z 295.1 (M + 1+). MS(−ESI)m/z 293.0 (M − 1+). |
| XO-B403 | | 5.98 | — | 62.1% (10 mg/kg) | 1H NMR(200 MHz) δ (DMSO-d6); 3.84 (3 H, s), 7.04 (1 H, ddd, J = 1, 7, 7 Hz), 7.14 (1 H, d, J = 8 Hz), 7.37 (1 H, ddd, J = 2, 7, 8 Hz), 7.49 (1 H, dd, J = 2, 7 Hz), 7.82 (1 H, d, J = 2 Hz), 7.86 (2 H, d, J = 9 Hz), 8.07 (2 H, d, J = 9 Hz), 8.43 (1 H, d, J = 2 Hz), 13.13 (1 H, brs). MS(+ESI)m/z 319.1 (M + 1+). MS(−ESI)m/z 317.1 (M − 1+). |
| XO-B407 | | 4.73 | 55.5 | 76.9% (10 mg/kg) | 1H NMR(200 MHz) δ (DMSO-d6); 2.30 (3 H, s), 7.04 (1 H, d, J = 5 Hz), 7.50 (1 H, d, J = 5 Hz), 7.83 (1 H, d, J = 2 Hz), 7.88 (2 H, d, J = 9 Hz), 8.07 (2 H, d, J = 9 Hz), 8.50 (1 H, d, J = 2 Hz). MS(+ESI)m/z 309.1 (M + 1+). MS(−ESI)m/z 307.1 (M − 1+). |
| XO-B410 | | 5.00 | — | 59.1% (10 mg/kg) | 1H NMR(200 MHz) δ (DMSO-d6); 3.72 (3 H, s), 6.09 (1 H, dd, J = 3, 4 Hz), 6.33 (1 H, dd, J = 2, 4 Hz), 6.87 (1 H, dd, J = 2, 2 Hz), 7.80 (1 H, d, J = 2 Hz), 7.88 (2 H, d, J = 9 Hz), 8.07 (2 H, d, J = 9 Hz), 8.46 (1 H, d, J = 2 Hz). MS(+ESI)m/z 292.1 (M + 1+). MS(−ESI)m/z 290.1 (M − 1+). |

TABLE 11-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-B412 | | 6.38 | 50.5 | — | 1H NMR(200 MHz) δ (DMSO-d6); 7.57 (1 H, d, J = 7 Hz), 7.62-7.73 (1 H, m), 7.73-7.81 (2 H, m), 7.85 (2 H, d, J = 9 Hz), 7.88-7.94 (1 H, m), 8.07 (2 H, d, J = 9 Hz), 8.51 (1 H, d, J = 2 Hz). MS(+ESI)m/z 357.1 (M + 1+). MS(−ESI)m/z 355.1 (M − 1+). |
| XO-B414 | | 5.86 | — | 67.1% (10 mg/kg) | 1H NMR(200 MHz) δ (DMSO-d6); 7.19 (1 H, d, J = 4 Hz), 7.28 (1 H, d, J = 4 Hz), 7.86 (2 H, d, J = 9 Hz), 8.07 (2 H, d, J = 9 Hz), 8.09 (1 H, d, J = 2 Hz), 8.51 (1 H, d, J = 2 Hz). MS(+ESI)m/z 329.0 (M + 1+). 331.0 (M + 2 + 1+). MS(−ESI)m/z 327.0 (M − 1+). 329.0 (M + 2 − 1+). |

TABLE 12

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-B418 | | 4.63 | 62.6 | 79.1% (10 mg/kg) | 1H NMR(200 MHz) δ (DMSO-d6); 7.54 (1 H, dd, J = 1, 5 Hz), 7.69 (1 H, dd, J = 3, 5 hz), 7.78 (1 H, dd, J = 1, 3 Hz), 7.87 (2 H, d, J = 9 Hz), 8.08 (2 H, d, J = 9 Hz), 8.12 (1 H, d, J = 2 Hz), 8.47 (1 H, d, J = 2 Hz), 13.14 (1 H, brs). MS(+ESI)m/z 295.1 (M + 1+). MS(−ESI)m/z 293.1 (M − 1+). |
| XO-B420 | | 6.33 | — | — | 1H NMR(200 MHz) δ (DMSO-d6); 7.76 (1 H, d, J = 3 Hz), 7.91 (2 H, dd, J = 2, 7 Hz), 7.92 (1 H, d, J = 3 Hz), 8.07 (2 H, dd, J = 2, 7 Hz), 8.34 (1 H, d, J = 2 Hz), 8.56 (1 H, d, J = 2 Hz). MS(+ESI)m/z 296.1 (M + 1+). MS(−ESI)m/z 294.0 (M − 1+). |
| XO-B421 | | 5.71 | — | 57.8% (10 mg/kg) | 1H NMR(200 MHz) δ (DMSO-d6); 7.56 (2 H, dd, J = 2, 7 Hz), 7.77 (2 H, dd, J = 2, 7 Hz), 7.89 (2 H, d, J = 9 Hz), 8.08 (2 H, d, J = 9 Hz), 8.16 (1 H, d, J = 2 Hz), 8.52 (1 H, d, J = 2 Hz). MS(+ESI)m/z 323.1 (M + 1+), 325.1 (M + 2 + 1+). MS(−ESI)m/z 321.1 (M − 1+), 323.1 (M + 2 − 1+). |

TABLE 12-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-B422 | | 3.56 | — | 79.0% (10 mg/kg) | 1H NMR(200 MHz) δ (DMSO-d6); 3.80 (3 H, s), 7.05 (2 H, dd, J = 2, 7 Hz), 7.67 (2 H, dd, J = 2, 7 Hz), 7.88 (2 H, d, J = 9 Hz), 8.01 (1 H, d, J = 2 Hz), 8.07 (2 H, d, J = 9 Hz), 8.47 (1 H, d, J = 2 Hz). MS(+ESI)m/z 319.1 (M + 1+). MS(−ESI)m/z 317.1 (M − 1+). |
| XO-B423 | | 4.26 | — | 66.6% (10 mg/kg) | 1H NMR(200 MHz) δ (DMSO-d6); 7.29 (2 H, d, J = 8 Hz), 7.63 (2 H, d, J = 8 Hz), 7.88 (2 H, d, J = 9 Hz), 8.05 (1 H, d, J = 2 Hz), 8.07 (2 H, d, J = 9 Hz), 8.48 (1 H, d, J = 2 Hz). MS(+ESI)m/z 303.1 (M + 1+). MS(−ESI)m/z 301.1 (M − 1+). |
| XO-B428 | | 5.09 | — | 68.3% (10 mg/kg) | 1H NMR(200 MHz) δ (DMSO-d6); 7.86 (2 H, d, J = 8 Hz), 7.87 (2 H, d, J = 9 Hz), 7.97 (2 H, d, J = 8 Hz), 8.08 (2 H, d, J = 9 Hz), 8.27 (1 H, d, J = 2 Hz), 8.55 (1 H, d, J = 2 Hz). MS(+ESI)m/z 357.1 (M + 1+). MS(−ESI)m/z 355.1 (M − 1+). |
| XO-B434 | | 3.82 | 68.8 | 63.2% (10 mg/kg) | 1H NMR(200 MHz) δ (DMSO-d6); 4.28 (4 H, s), 6.95 (1 H, d, J = 8 Hz), 7.21 (1 H, dd, J = 2, 8 Hz), 7.25 (1 H, d, J = 2 Hz), 7.88 (2 H, d, J = 9 Hz), 8.02 (1 H, d, J = 2 Hz), 8.07 (2 H, d, J = 9 Hz), 8.46 (1 H, d, J = 2 Hz), 13.15 (1 H, brs). MS(+ESI)m/z 347.1 (M + 1+). MS(−ESI)m/z 345.1 (M − 1+). |
| XO-B436 | | 3.71 | — | 77.3% (10 mg/kg) | 1H NMR(200 MHz) δ (DMSO-d6); 7.28-7.53 (3 H, m), 7.68 (1 H, ddd, J = 2, 8, 8 Hz), 7.88 (2 H, d, J = 9 Hz), 7.95 (1 H, dd, J = 1, 2 Hz), 8.08 (2 H, d, J = 9 Hz), 8.54 (1 H, d, J = 2 Hz). MS(+ESI)m/z 307.1 (M + 1+). MS(−ESI)m/z 305.1 (M − 1+). |
| XO-B438 | | 5.03 | — | 69.3% (10 mg/kg) | 1H NMR(200 MHz) δ (DMSO-d6); 7.32 (2 H, dd, J = 2, 7 Hz), 7.36 (2 H, dd, J = 2, 7 Hz), 7.76 (2 H, dd, J = 2, 7 Hz), 7.78 (2 H, dd, J = 2, 7 Hz), 7.89 (2 H, d, J = 9 Hz), 8.08 (2 H, d, J = 9 Hz), 8.10 (1 H, d, J = 2 Hz), 8.51 (1 H, d, J = 2 Hz). MS(+ESI)m/z 307.1 (M + 1+). MS(−ESI)m/z 305.1 (M − 1+). |

TABLE 12-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-B440 | | 15.2 | — | 57.6% (10 mg/kg) | 1H NMR(200 MHz) δ (DMSO-d6); 2.20 (3 H, s), 7.32-7.56 (5 H, m), 7.66 (2 H, dd, J = 2, 7 Hz), 7.99 (1 H, s), 8.11 (2 H, dd, J = 2, 7 Hz), 13.20 (1 H, brs). MS(+ESI)m/z 303.1 (M + 1+). MS(−ESI)m/z 301.1 (M − 1+). |

TABLE 13

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-CH146 | | 50.5 | 92.1 | — | 1H NMR(200 MHz) δ (DMSO-d6); 7.34-7.48 (2 H, m), 7.65-7.80 (2 H, m), 7.82 (2 H, d, J = 8 Hz), 8.17 (2 H, d, J = 8 Hz), 8.70 (1 H, s), 13.25 (1 H, brs). |
| XO-CH160 | | 26.7 | 93.8 | — | 1H NMR(200 MHz) δ (DMSO-d6); 7.43 (1 H, dd, J = 9 Hz, 2 Hz), 7.71 (1 H, d, J = 9 Hz), 7.75-7.86 (3 H, m), 8.17 (2 H, dd, J = 9 Hz, 2 Hz), 8.77 (1 H, s). MS(−ESI)m/z 297, 295 (+ESI)m/z 299, 297 |
| XO-CH168 | | 57.1 | 92.5 | — | 1H NMR(200 MHz) δ (DMSO-d6); 7.28 (1 H, ddd, J = 9 Hz, 9 Hz, 3 H), 7.59 (1 H, dd, J = 9 Hz, 3 Hz), 7.72 (1 H, dd, J = 9 Hz, 4 Hz), 7.81 (2 H, d, J = 9 Hz), 8.17 (2 H, d, J = 9 Hz), 8.76 (1 H, s), 13.19 (1 H, brs). |

TABLE 13-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-CH164 | | 13.8 | 92.3 | 51.4% (50 mg/kg) | 1H NMR(200 MHz) δ (DMSO-d6); 2.47 (3 H, s), 7.24 (1 H, dd, J = 9 Hz, 2 Hz), 7.56 (1 H, s), 7.60 (1 H, d, J = 9 Hz), 7.79 (2 H, d, J = 9 Hz), 8.16 (2 H, d, J = 9 Hz), 8.63 (1 H, s), 13.21 (1 H, brs).<br>MS(−ESI)m/z 275 (+ESI)m/z 277, 299 |
| XO-CH150 | | 31.6 | 79.3 | — | 1H NMR(200 MHz) δ (DMSO-d6); 7.32-7.48 (2 H, m), 7.67-7.83 (2 H, m), 7.94 (2 H, d, J = 9 Hz,), 8.28 (2 H, d, J = 9 Hz,), 8.71 (1 H, s).<br>MS(EI)m/z 286 (M+), 258 |
| XO-CH151 | | — | — | — | 1H NMR(200 MHz) δ (DMSO-d6); 7.05 (1 H, brs), 7.20-7.48 (2 H, m), 7.60 (1 H, brs), 7.60-7.70 (1 H, m), 7.90 (2 H, d, J = 9 Hz), 8.22-8.35 (3 H, m), 8.43 (1 H, s).<br>MS(EI)m/z 304 (M+), 276 |
| XO-CH172 | | — | 88.3 | — | 1H NMR(200 MHz) δ (DMSO-d6); 2.46 (3 H, s), 7.10-7.37 (3 H, m), 7.62-7.70 (1 H, m), 7.69 (2 H, d, J = 8 Hz), 8.19 (2 H, d, J = 8 Hz), 13.31 (1 H, brs).<br>MS(−ESI)m/z 275 (+ESI)m/z 277 |
| XO-CH183 | | 14.5 | 80.6 | — | 1H NMR(200 MHz) δ (DMSO-d6); 3.86 (3 H, s), 7.02 (1 H, dd, J = 9 Hz, 2 Hz), 7.21 (1 H, d, J = 2 Hz), 7.62 (1 H, d, J = 9 Hz), 7.79 (2 H, d, J = 9 Hz), 8.15 (2 H, d, J = 9 Hz), 8.62 (1 H, s), 13.23 (1 H, brs).<br>MS(−ESI)m/z 291 (+ESI)m/z 293 |

TABLE 13-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-CH199 | | 49.1 | 91.5 | — | 1H NMR(200 MHz) δ (DMSO-d6); 6.12 (2 H, s), 7.23 (1 H, s), 7.24 (1 H, s), 7.78 (2 H, d, J = 9 Hz), 8.16 (2 H, d, J = 9 Hz), 8.48 (1 H, s). MS(−ESI)m/z 305 (+ESI)m/z 307 |

TABLE 14

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-CH200 | | 76.2 | 94.3 | — | 1H NMR(200 MHz) δ (DMSO-d6); 3.80 (3 H, s), 7.03 (1 H, dd, J = 9 Hz, 2 Hz), 7.13 (1 H, d, J = 2 Hz), 7.65 (1 H, d, J = 9 Hz), 7.82 (2 H, d, J = 9 Hz), 8.17 (2 H, d, J = 9 Hz), 8.54 (1 H, s), 13.22 (1 H, brs). MS(−ESI)m/z 291 (+ESI)m/z 293 |
| XO-CH201 | | 50.5 | 88.6 | — | 1H NMR(200 MHz) δ (DMSO-d6); 7.30-7.49 (2 H, m), 7.64 (1 H, dd, J = 7 Hz, 2 Hz), 7.81 (2 H, d, J = 9 Hz), 8.17 (2 H, d, J = 9 Hz), 8.81 (1 H, s), 13.27 (1 H, brs). MS(−ESI)m/z 295, 297 (+ESI)m/z 297, 299 |
| XO-CH205 | | — | 95.7 | — | 1H NMR(200 MHz) δ (DMSO-d6); 1.95 (3 H, s), 7.13 (1 H, d, J = 7 Hz), 7.26 (1 H, dd, J = 8 Hz, 7 Hz), 7.59 (1 H, d, J = 8 Hz), 7.69 (2 H, d, J = 8 Hz), 8.11 (2 H, d, J = 8 Hz), 8.41 (1 H, s), 13.30 (1 H, brs). MS(−ESI)m/z 275 (+ESI)m/z 277 |

TABLE 14-continued

| Compound | Structural Formula | X.O. inhibition IC50 (nmol/L) | URAT1 (100 μmol/L) (%) inhibition | Decrease (%) in UA concentration | Physical Data |
|---|---|---|---|---|---|
| XO-CH206 | | — | 98.1 | — | 1H NMR(200 MHz) δ (DMSO-d6); 7.71 (1 H, d, J = 9 Hz), 7.86 (2 H, d, J = 9 Hz), 7.92 (1 H, s), 8.02 (1 H, d, J = 8 Hz), 8.20 (2 H, d, J = 9 Hz), 8.92 (1 H, s), 13.29 (1 H, brs). MS(−ESI)m/z 329 (+ESI)m/z 331 |
| XO-CH207 | | 96.5 | 93.9 | — | 1H NMR(200 MHz) δ (DMSO-d6); 3.80 (3 H, s), 7.03 (1 H, dd, J = 9 Hz, 2 Hz), 7.13 (1 H, d, J = 2 Hz), 7.65 (1 H, d, J = 9 Hz), 7.82 (2 H, d, J = 9 Hz), 8.17 (2 H, d, J = 9 Hz), 8.54 (1 H, s), 13.22 (1 H, brs). MS(−ESI)m/z 291 (+ESI)m/z 293 |
| XO-CH209 | | 60.8 | 97.1 | — | 1H NMR(200 MHz) δ (DMSO-d6); 7.43 (1 H, dd, J = 9 Hz, 2 Hz), 7.72 (1 H, d, J = 2 Hz), 7.80 (1 H, d, J = 9 Hz), 7.82 (2 H, d, J = 9 Hz), 8.17 (2 H, d, J = 9 Hz), 8.74 (1 H, s), 13.26 (1 H, brs). MS(−ESI)m/z 295, 297 (+ESI)m/z 297, 299 |
| XO-CH211 | | 16.4 | 81.1 | — | 1H NMR(200 MHz) δ (DMSO-d6); 3.96 (3 H, s), 6.88 (1 H, d, J = 8 Hz), 7.24 (1 H, d, J = 8 Hz), 7.28-7.41 (1 H, m), 7.78 (2 H, d, J = 9 Hz), 8.16 (2 H, d, J = 9 Hz), 8.56 (1 H, s), 13.22 (1 H, brs). MS(−ESI)m/z 291 (+ESI)m/z 293 |
| XO-KT10 | | — | 92.3 | — | 1H NMR(200 MHz) δ (DMSO-d6); 7.48 (1 H, dd, J = 8 Hz, 5 Hz), 8.05-8.18 (4 H, m), 8.29 (1 H, dd, J = 8 Hz, 2 Hz), 8.53 (1 H, dd, J = 5 Hz, 2 Hz), 13.2 (1 H, brs). |

TABLE 14-continued

| Compound | Structural Formula | X.O. inhibition IC50 (nmol/L) | URAT1 (100 μmol/L) (%) inhibition | Decrease (%) in UA concentration | Physical Data |
| --- | --- | --- | --- | --- | --- |
| XO-KT16 | | 99.2 | 92.4 | — | 1H NMR(200 MHz) δ (DMSO-d6); 8.00-8.17 (4 H, m), 8.16 (1 H, d, J = 2.2 Hz), 8.58 (1 H, d, J = 2.2 Hz), 9.05 (1 H, s), 13.2 (1 H, s). |

TABLE 15

| Compound | Structural Formula | X.O. inhibition IC50 (nmol/L) | URAT1 (100 μmol/L) (%) inhibition | Decrease (%) in UA concentration | Physical Data |
| --- | --- | --- | --- | --- | --- |
| XO-KT18 | | — | 95.2 | — | 1H NMR(200 MHz) δ (DMSO-d6); 7.54 (1 H, d, J = 8.3 Hz), 7.96-8.19 (4 H, m), 8.35 (1 H, d, J = 8.3 Hz), 9.00 (1 H, s), 13.2 (1 H, brs). |
| XO-KT20 | | — | 64.6 | — | 1H NMR(200 MHz) δ (DMSO-d6); 7.99~8.19 (4 H, m), 8.94 (2 H, dd, J = 1.9 Hz, 5.9 Hz), 9.19 (1 H, s), 13.3 (1 H, brs). |
| XO-KT30 | | — | 79.9 | — | 1H NMR(200 MHz) δ (DMSO-d6); 7.53-7.77 (2 H, m), 7.98-8.22 (6 H, m), 13.3 (1 H, brs). |

INDUSTRIAL APPLICABILITY

The nitrogen-containing heterocyclic compounds or the present invention or the pharmaceutically acceptable salts thereof are compounds having a X.O. inhibitory effect and an uricosuric effect. The pharmaceutical compositions of the present invention comprising these compounds as an active ingredient can be expected to be useful as a therapeutic agent for the gout or hyperuricemia, or various diseases such as ischemic-reperfusion disorder, inflammatory disease, diabetes, cancer, arteriosclerosis, neurological disease or the like.

The invention claimed is:

1. A nitrogen-containing heterocyclic compound represented by the following general formula (I):

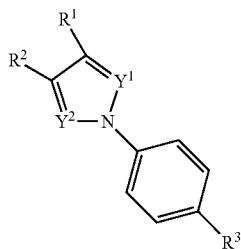

(I)

wherein $Y^1$ represents N or $C(R^4)$; $Y^2$ represents N or $C(R^5)$; $R^4$ and $R^5$ independently represents an alkyl group which may have a halogen atom, a hydrogen atom, a halogen atom, a cyano group or an alkoxy group; one of $R^1$ and $R^2$ represents an haloalkyl group, a cyano group, a carbamoyl group or a halogen atom; the other of $R^1$ and $R^2$ represents an aryl group which may have a substituent selected from the group consisting of an alkyl group, a haloalkyl group, an alkoxy group and a halogen atom, wherein the substituents on the aryl group of $R^1$ or $R^2$ may form a ring selected from the group consisting of a dioxolane and a dioxane, an alkoxy group or a heterocyclic group selected from the group consisting of a thienyl, thiazolyl or pyrrolyl group which may be substituted by an alkyl group or a halogen atom; and $R^3$ represents a 5-tetrazolyl group or a carboxy group; and with the proviso that when $Y^2$ represents $CR^5$, $Y^2$ may form, together with $R^2$, a benzene or pyridine ring which may have a haloalkyl group, a halogen atom, a cyano group or an alkoxy group as a substituent, and the neighboring substituents on the benzene or pyridine ring may form a ring selected from the group consisting of a diaxololane and a dioxane, or a pharmaceutically acceptable salt thereof.

2. A nitrogen-containing heterocyclic compound as claimed in claim 1 represented by the following general formula (I-A) or (I-B):

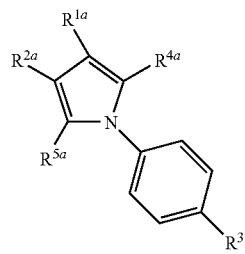

(I-A)

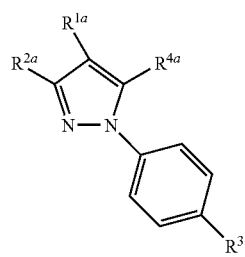

(I-B)

wherein $R^{4a}$ and $R^{5a}$ independently represent a hydrogen atom or an alkyl group;

one of $R^{1a}$ and $R^{2a}$ represents a haloalky group, a cyano group or a halogen atom;

the other of $R^{1a}$ and $R^{2a}$ represents an aryl group which may have a substituent selected from the group consisting of an alkyl group, a haloalkyl group, an alkoxy group and a halogen atom, wherein the substituents on the aryl group of $R^{1a}$ or $R^{2a}$ may form a ring selected from the group consisting of a dioxolane and a dioxane, an alkoxy group or a heterocyclic group selected from the group consisting of a thienyl, thiazolyl or pyrrolyl group which may be substituted by an alkyl group or a halogen atom; and $R^3$ represents a 5-tetrazolyl group or a carboxy group, or a pharmaceutically acceptable salt thereof.

3. A nitrogen-containing heterocyclic compound as claimed in claim 2, wherein $R^{1a}$ represents a cyano group, or a pharmaceutically acceptable salt thereof.

4. A nitrogen-containing heterocyclic compound as claimed in claim 3, wherein $R^{2a}$ represents an aryl group which may have a substituent selected from the group consisting of an alkyl group, a haloalkyl group, an alkoxy group and a halogen atom in which some of the substituents may form a ring; an alkoxy group; or a thienyl group which may be substituted by an alkyl group or a halogen atom, or a pharmaceutically acceptable salt thereof.

5. A nitrogen-containing heterocyclic compound as claimed in claim 2, wherein $R^3$ represents a carboxy group, or a pharmaceutically acceptable salt thereof.

6. A nitrogen-containing heterocyclic compound as claimed in claim 1 represented by the following general formula (I-C):

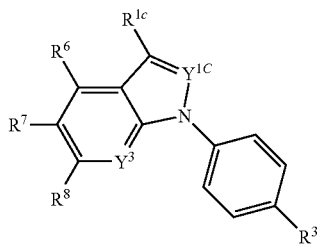

(I-C)

wherein $y^{1C}$ represents N or C ($R^{4C}$); $Y^3$ represents N or C($R^9$); $R^{4C}$ and $R^9$ independently represent an alkyl group, a haloalkyl group, a hydrogen atom, a halogen atom, a cyano group or an alkoxy group;

$R^{1C}$ represents a cyano group or a carbamoyl group;

$R^6$, $R^7$ and $R^8$ independently represent an alkyl group, a haloalkyl group, a hydrogen atom, a halogen atom, a cyano group or an alkoxy group; or any of $R^6$, $R^7$ and $R^8$ may form a ring selected from the group consisting of a dioxolane and a dioxane together with the neighboring substituent; and $R^3$ represents a 5-tetrazolyl group or a carboxy group, or a pharmaceutically acceptable salt thereof.

7. A nitrogen-containing heterocyclic compound as claimed in claim 6, wherein $R^{1C}$ represents a cyano group, or a pharmaceutically acceptable salt thereof.

8. A nitrogen-containing heterocyclic compound as claimed in claim 6, wherein $R^3$ represents a carboxy group, or a pharmaceutically acceptable salt thereof.

9. A pharmaceutical composition comprising a nitrogen-containing heterocyclic compound as claimed in claim 1 or a pharmaceutically acceptable salt thereof as an active ingredient.

10. A pharmaceutical composition as claimed in claim 9, which is a xanthine oxidase inhibitor.

11. A pharmaceutical composition as claimed in claim 9, which is an uricosuric agent.

12. A pharmaceutical composition as claimed in claim 9, which is an agent for the treatment of gout or hyperuricemia.

* * * * *

UNITED STATES PATENT AND TRADEMARK OFFICE
CERTIFICATE OF CORRECTION

| | | |
|---|---|---|
| PATENT NO. | : 7,947,707 B2 | Page 1 of 1 |
| APPLICATION NO. | : 12/089518 | |
| DATED | : May 24, 2011 | |
| INVENTOR(S) | : Takahiro Toyoshima et al. | |

It is certified that error appears in the above-identified patent and that said Letters Patent is hereby corrected as shown below:

Column 79, line 63, the term "diaxololane" should be --dioxolane--.

Column 81, line 14, the term "$y^{1C}$" should be --$Y^{1C}$--.

Signed and Sealed this

Fourth Day of October, 2011

David J. Kappos
*Director of the United States Patent and Trademark Office*